(12) United States Patent
Gosink et al.

(10) Patent No.: US 11,317,805 B2
(45) Date of Patent: May 3, 2022

(54) WEARABLE HEALTH MONITORING DEVICE

(71) Applicant: Battelle Memorial Institute, Richland, WA (US)

(72) Inventors: Luke J. Gosink, Richland, WA (US); Sean McNeil, Richland, WA (US); Juan M. Brandi-Lozano, Richland, WA (US); Ryan Williams, Richland, WA (US); Joseph R. Bruce, Richland, WA (US); Jonathon D. McCall, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 918 days.

(21) Appl. No.: 16/039,135

(22) Filed: Jul. 18, 2018

(65) Prior Publication Data

US 2019/0076024 A1 Mar. 14, 2019

Related U.S. Application Data

(60) Provisional application No. 62/624,378, filed on Jan. 31, 2018, provisional application No. 62/558,185, filed on Sep. 13, 2017.

(51) Int. Cl.
*A61B 5/021* (2006.01)
*A61B 5/00* (2006.01)
(Continued)

(52) U.S. Cl.
CPC .......... *A61B 5/0024* (2013.01); *A61B 5/0006* (2013.01); *A61B 5/0205* (2013.01);
(Continued)

(58) Field of Classification Search
CPC ......... A61B 5/00; A61B 5/0205; A61B 5/746; A61B 5/0006; A61B 5/0024; A61B 5/352;
(Continued)

(56) References Cited

U.S. PATENT DOCUMENTS 5,309,916 A * 5/1994 Hatschek ............... A61B 5/021
600/485
5,865,755 A 2/1999 Golub
(Continued)

FOREIGN PATENT DOCUMENTS

EP 1424037 6/2006

OTHER PUBLICATIONS

International Preliminary Report on Patentability received in PCT/US2018/042736, dated Mar. 17, 2020, 6 pages.
(Continued)

*Primary Examiner* — Eric J Messersmith
(74) *Attorney, Agent, or Firm* — Klarquist Sparkman, LLP

(57) ABSTRACT

A wearable patient device is provided that includes one or more sensors. The one or more sensors can record one or both of ECG information or phonocardiographic information. The sensor information can be used to determine the blood pressure of a monitored individual, including on a continuous basis. Blood pressure can be determined using one or both of a determined time to empty or fill one or more heart chambers or first and second blood velocities. Vital sign information can be provided to a monitoring individual, including graphical representations of trend information.

21 Claims, 12 Drawing Sheets

(51) Int. Cl.
  *A61B 5/0205* (2006.01)
  *A61B 5/352* (2021.01)
(52) U.S. Cl.
  CPC .............. *A61B 5/352* (2021.01); *A61B 5/681* (2013.01); *A61B 5/746* (2013.01); *A61B 5/021* (2013.01); *A61B 2562/0219* (2013.01)
(58) Field of Classification Search
  CPC .. A61B 5/681; A61B 5/021; A61B 2562/0219
  See application file for complete search history.

(56) References Cited

U.S. PATENT DOCUMENTS

| | | | |
|---|---|---|---|
| 8,585,605 B2* | 11/2013 | Sola I Caros | A61B 5/029 600/506 |
| 2002/0082507 A1* | 6/2002 | Kolluri | A61B 5/318 600/485 |
| 2005/0261593 A1 | 11/2005 | Zhang et al. | |
| 2008/0082004 A1 | 4/2008 | Banet et al. | |
| 2010/0160798 A1 | 6/2010 | Banet et al. | |
| 2011/0208016 A1* | 8/2011 | Bombardini | A61B 5/021 600/301 |
| 2013/0297538 A1 | 11/2013 | Gosink et al. | |
| 2016/0022224 A1 | 1/2016 | Banet et al. | |
| 2016/0353998 A1 | 12/2016 | Lee et al. | |

OTHER PUBLICATIONS

"Chest Based Pulse Oximetry Device," UK Research and Innovation, Abstract only, retrieved from: https://gtr.ukri.org/projects?ref=710126, 3 pages.
"Chest Mounted Pulse Oximetry," MEDICA Magazine, Sep. 17, 2007, retrieved from: https://www.medica-tradefair.com/cgi-bin/md_medica/lib/pub/tt.cgi/Chest_Mounted_Pulse_Oximetry.html?oid=22312&lang=2&ticket=g_u_e_s_t, 1 page.
"Fluid Mechanics for Gravity—Flow Water Systems and Pumps," Part 6. Imperfect Systems—Friction and the Bernoulli Equation, retrieved from: https://www.itacanet.org/fluid-mechanics-for-gravity-flow-water-systems-and-pumps/part-6-imperfect-systems-friction-and-the-bernoulli-equation/, 4 pages.
"Heart Sounds," ScienceDirect, Essential Emergency Medicine, 2007, retrieved from https://www.sciencedirect.com/topics/medicine-and-dentistry/heart-sounds, 10 pages.
"How does Bernoulli's Principle apply to the cardiovascular system?" StackExchange, retrieved from: https://biology.stackexchange.com/questions/36443/how-does-bernoulli-s-principle-apply-to-the-cardiovascular-system, 4 pages.
"Recurrent neural network," Wikipedia, https://en.wikipedia.org/wiki/Recurrent_neural_network, 16 pages.
Basics of hemodynamics, retrieved from: http://www.blackwellpublishing.com/content/BPL_Images/Content_store/Sample_Chapter/9781405169172/9781405169172_4_001.pdf, Aug. 1, 2007, 16 pages.
Bernoulli equation, Wikilectures, Dec. 14, 2014, retrieved from: https://www.wikilectures.eu/w/Bernoulli_equation, 3 pages.
Bernoulli's Equation, retrieved from: https://www.princeton.edu/~asmits/Bicycle_web/Bernoulli.html, 4 pages.
Chua et al., "Sound Based Heart Rate Monitoring for Wearable Systems," 2010 *International Conference on Body Sensor Networks*, IEEE, 2010, Abstract only, retrieved from: https://www.computer.org/csdl/proceedings/bsn/2010/4065/00/4065a139.pdf, 2 pages.
Debbral et al., "Frequency analysis of the heartbeat sounds," Biomedical Soft Computing and Human Sciences, vol. 13, No. 1, pp. 85-90 (2008).
Ding et al., "Pulse Transit Time Based Continuous Cuffless Blood Pressure Estimation: A New Extension and a Comprehensive Evaluation," Sci Rep, 2017, retrieved from: https://www.ncbi.nlm.nih.gov/pmc/articles/PMC5599606/, 11 pages.

ELR 4202C Project: Heart Sound Pulse Display Module, retrieved from http://web.eng.fiu.edu/watsonh/ELR4202/Project/HeartSounds.pdf, 12 pages.
Erbel et al., "Aortic Dimensions and the Risk of Dissection," Heart 2006; 92:137-142, retrieved from: https://www.ncbi.nlm.nih.gov/pmc/articles/PMC1861012/pdf/137.pdf.
Gao et al., "Comparison of noninvasive pulse transit time estimates as markers of blood pressure using invasive pulse transit time measurements as a reference," Physiological Reports, ISSN 2051-817X, vol. 4, Issue 10, 2016, 7 pages.
Healthcare IOT, Maxim Integrated, retrieved from: https://www.maximintegrated.com/en/markets/healthcare/healthcare-iot.html, 6 pages.
Hemodynamics, Bernoulli's principle, Echocardiografie, retrieved from http://echocardiografie.nl/hemodynamics/, 9 pages.
Holzner, "Use Bernoulli's Equation to Calculate Pressure Difference Between Two Points," retrieved from: https://www.dummies.com/education/science/physics/use-bernoullis-equation-to-calculate-pressure-difference-between-two-points/, 6 pages.
International Search Report received in PCT/US2018/042736, dated Nov. 25, 2018, 7 pages.
Lee et al., "Reflectance pulse oximetry: Practical issues and limitations," ICT Express 2 (2016) retrieved from: https://reader.elsevier.com/reader/sd/pii/S2405959516301205?token=7CDC47611DE8A3A7BBB21D23B100400EA65F8EA15FBD5521316ABDA383A62DFE4E6D0B4EF33DD0092BD9B31E7AA7BAD7, 4 pages.
Maceira et al., "Normalized Left Ventricular Systolic and Diastolic Function by Steady State Free Precession Cardiovascular Magnetic Resonance," Journal of Cardiovascular Magnetic Resonance (2006) 8, 417-426.
MAX30001 Ultra-Low-Power, Single-Channel Integrated Biopotential (ECG, R-to-R and Pace Detection and Bioimpedance (BioZ) AFE, retrieved from: https://www.maximintegrated.com/en/products/analog/data-converters/analog-front-end-ics/MAX30001.html, 7 pages.
MAX30004 Ultra-Low Power, Single-Channel Integrated Biopotential HR Detection AFE, retrieved from: https://www.maximintegrated.com/en/products/analog/data-converters/analog-front-end-ics/MAX30004.html, 4 pages.
MAX30110 Optimized Pulse-Oximeter and Heath Rate AFE for Wearable Health, retrieved from: https://www.maximintegrated.com/en/products/analog/data-converters/analog-front-end-ics/MAX30110.html, 5 pages.
MAX30112 Optimized Pulse-Oximeter and Heath Rate AFE for Wearable Health, retrieved from: https://www.maximintegrated.com/en/products/sensors/MAX30112.html, 5 pages.
MAX86140 Best-in-Class Optical Pulse Oximeter and Heart-Rate Sensor for Wearable Health, retrieved from: https://www.maximintegrated.com/en/products/sensors/MAX86140.html, 6 pages.
MAXREFDES100#: Health Sensor Platform, retrieved from: https://www.maximintegrated.com/en/design/reference-design-center/system-board/6312.html, 5 pages.
Muehlsteff et al., "Pulse Arrival Time as surrogate for systolic blood pressure changes during impending nerually mediated syncope," Conf Proc IEEE Eng Med Biol Soc. 2012;2012:4283-6. doi: 10.1109/EMBC.2012.6346913, Abstract only, retrieved from: https://www.ncbi.nlm.nih.gov/pubmed/23366874, 1 page.
Mutschler, et al., "The Shock Index revisited—a fast guide to transfusion requirement? A retrospective analysis on 21,853 patients derived from the TraumaRegister DGU," Retrieved from: https://ccforum.biomedcentral.com/track/pdf/10.1186/cc12851, 9 pages.
Patel, "Test Report Wireless Patient Vital Signs Monitoring Device Operational Field Assessment," National Urban Security Technology Laboratory, Department of Homeland Security Science and Technology Directorate First Responders Group, May 2014, 20 pages.
Patents Assigned to Sotera Wireless, Inc., retrieved from: https://patents.justia.com/assignee/sotera-wireless-inc?page=5, 11 pages.
Schreiner et al., "Blood Oxygen Level Measurement with a chest-based Pulse Oximetry Prototype System," Computing in Cardiology, 2010, 37:537-540, retrieved from https://ieeexplore.ieee.org/document/5738028.
The VISI Mobile System, All Vital Signs, All the Time, retrieved from http://www.soterawireless.com/visi-mobile/, 2 pages.

(56) References Cited

OTHER PUBLICATIONS

Visi Mobile Insight, Continuous vital sign monitoring system with custom wearable, retrieved from: https://reinvently.com/work/visi-mobile-insight/, 5 pages.

Visi Mobile Remote Viewer User Manual, Sortera Wireless, Feb. 2014, 166 pages.

Visi Mobile Surveillance Monitoring System, Sotera Wireless, http://www.soterawireless.com/wp-content/uploads/2016/01/New-6-000417-00_A-Large-format-ViSi-Brochure.pdf, 2 pages.

Visi Mobile Wearable Device, retrieved on Apr. 12, 2018 from: http://vandrico.com/wearables/device/visi-mobile, 3 pages.

Wang et al., "Cuff-Free Blood Pressure Estimation Using Pulse Transit Time and Heart Rate," Int Conf Signal Process Proc. Oct. 2014, retrieved from: https://www.ncbi.nlm.nih.gov/pmc/articles/PMC4512231/, 12 pages.

Westerhof, et al., "Bernoulli's Equation," Abstract only, retrieved from: https://link.springer.com/chapter/10.1007%2F978-1-4419-6363-5_3, Jul. 17, 2010, 3 pages.

Written Opinion received in PCT/US2018/042736, dated Nov. 25, 2018, 5 pages.

Zhang et al., "Cuff-less blood pressure measurement using pulse arrival time and a Kalman filter," *Journal of Micromechanics and Microengineering,* vol. 27, No. 2, Jan. 9, 2017, retrieved from: https://iopscience.iop.org/article/10.1088/1361-6439/27/2/024002/pdf, Abstract only, 3 pages.

Zhang, et al., "Sound Based Heart Rate Monitoring for Wearable Systems," International Conference on Body Sensor Networks (BSN), pp. 139-143, 2010.

\* cited by examiner

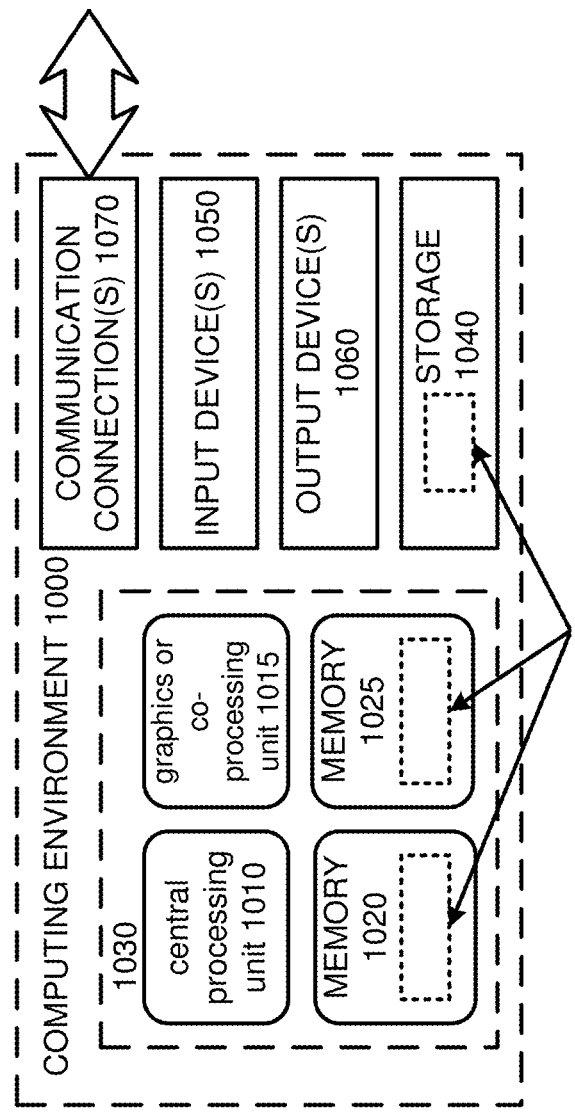

WEARABLE HEALTH MONITORING DEVICE

CROSS REFERENCE TO RELATED APPLICATIONS

This application claims the benefit of, and incorporates by reference, U.S. Provisional Application No. 62/624,378, filed Jan. 31, 2018, and U.S. Provisional Application No. 62/558,185, filed Sep. 13, 2017.

STATEMENT OF GOVERNMENT SUPPORT

This invention was made with Government support under Contract DE-AC05-76RL01830 awarded by the U.S. Department of Energy. The Government has certain rights in the invention.

BACKGROUND

While various diagnostic instruments exist to monitor an individual's vital signs, existing approaches can suffer from various drawbacks. For example, even with the advent of wearable technology, devices that are configured to be worn by an individual can be expensive, delicate, intrusive, or difficult to put on or take off. Further, typically a medical professional is called upon to review and interpret data. Particularly in situations such as a natural disaster or a busy emergency room, a limited number of medical personnel must oversee a number of patients who must be quickly triaged, treated, and monitored. It can be challenging for a medical professional to not only worry about installing and removing devices to monitor a patient's condition, but to simultaneously monitor the condition of multiple patients. Accordingly, room for improvement exists.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A wearable patient device is provided that includes one or more sensors. The one or more sensors can, for example, record one or both of electrocardiogram (ECG) information or phonocardiographic information. The sensor information can be used to determine the blood pressure of a monitored individual, including on a continuous basis. Blood pressure can be determined using one or both of (1) a determined time to empty or fill one or more heart chambers or (2) first and second blood velocities. Vital sign information can be provided to a monitoring individual, including graphical representations of trend information.

The disclosed technologies can provide various advantages. For example, blood pressure can be monitored using fewer patient sensors, which can increase the usability and durability of a patient monitoring device, as well as reducing its expense. Disclosed user interface screens can allow a monitoring individual to quickly view the status, including status changes, of a plurality of monitored individuals.

In one aspect, a method is provided for determining blood pressure of a monitored individual, such as on a continuous basis. Data is received from a hardware sensor coupled to a monitored individual. The hardware sensor records data associated with cardiac function of the monitored individual. A sensor coupled to the monitored individual refers to the hardware sensor being in sufficient physical proximity or contact with the monitored individual to obtain clinically useful readings from the sensor.

From the data, a time taken to fill one or more chambers of the heart with blood is determined. From the fill time, a blood pressure value is determined for the monitored individual. The blood pressure value is caused to be displayed to a monitoring individual.

In another aspect, another method is provided for determining blood pressure of a monitored individual, such as on a continuous basis. Data is received from a hardware sensor coupled to a monitored individual. The hardware sensor records data associated with cardiac function of the monitored individual. A sensor coupled to the monitored individual refers to the hardware sensor being in sufficient physical proximity or contact with the monitored individual to obtain clinically useful readings from the sensor.

From the data, a force associated with ejecting blood through a heart valve is determined. From the determined force, a blood pressure value for the monitored individual is determined. The blood pressure value is caused to be output for display to a monitoring individual.

In a further aspect, a computer-generated display of vital sign information is provided. The display includes a plurality of vital sign indicators, each identifying a type of monitored vital sign. A plurality of vital sign values are included in the display, proximate associated vital sign indicators, respectively. A plurality of vital sign trend indicators are included in the display, proximate associated vital sign indicators, respectively. The vital sign trend indicators each comprise a plot of vital sign values of a respective vital sign indicator over a time window.

The present disclosure also includes computing systems and computer readable storage media configured to carry out, or including instructions for carrying out, an above-described method. As described herein, a variety of other features and advantages can be incorporated into the technologies as desired.

BRIEF DESCRIPTION OF THE DRAWINGS

FIG. 10 is a diagram of an example computing system in which some described embodiments can be implemented.

DETAILED DESCRIPTION

Example 1

Overview

Figure 1:
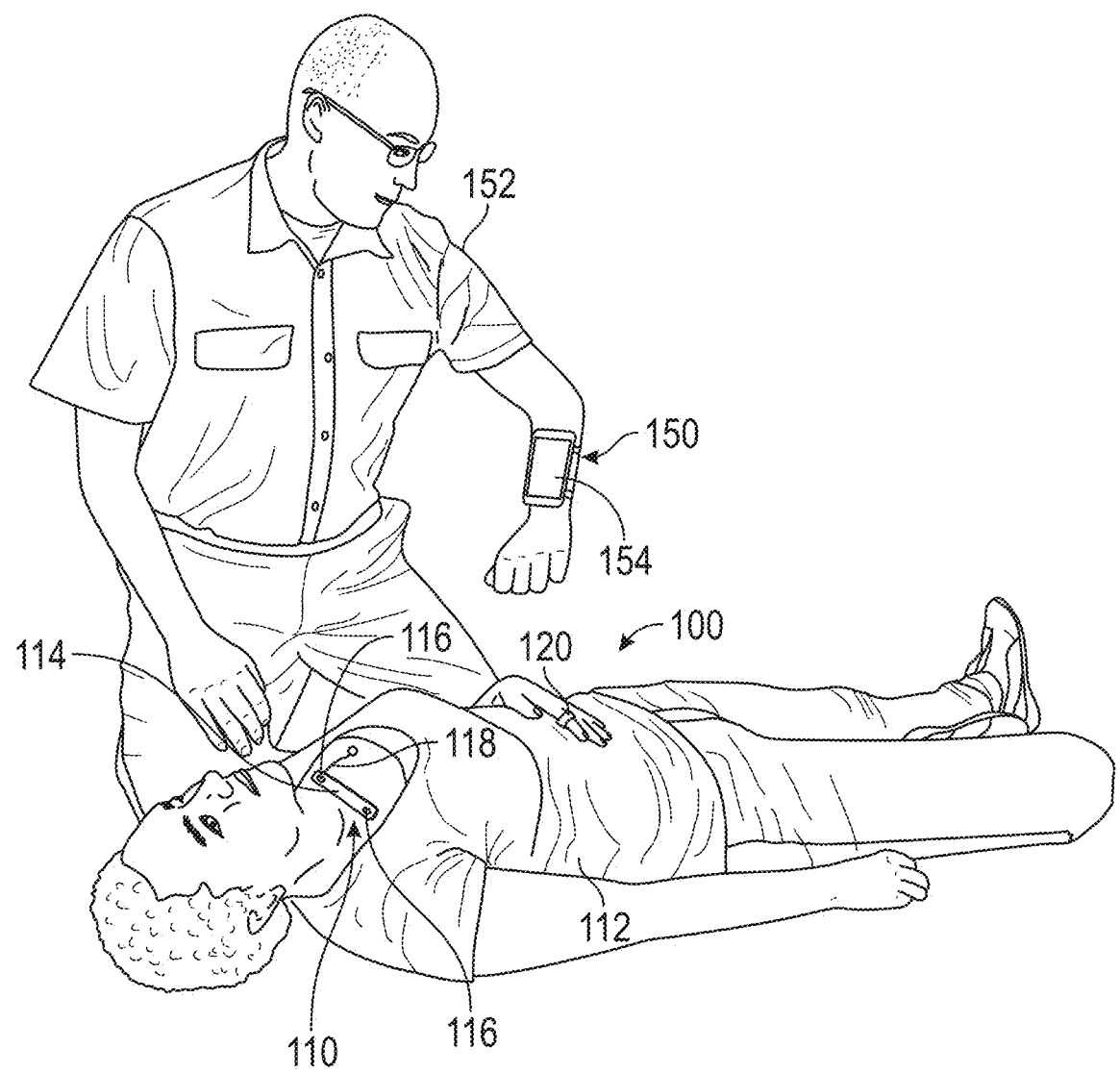
FIG. 1 is a depiction of a patient monitoring device and a provider device in an example use case scenario.

While various diagnostic instruments exist to monitor an individual's vital signs, existing approaches can suffer from various drawbacks. For example, even with the advent of wearable technology, devices that are configured to be worn by an individual can be expensive, delicate, intrusive, or difficult to put on or take off. Further, typically a medical professional is called upon to review and interpret data. Particularly in situations such as a natural disaster or a busy emergency room, a limited number of medical personnel must oversee a number of patients who must be quickly triaged, treated, and monitored. It can be challenging for a medical professional to not only worry about installing and removing devices to monitor a patient's condition, but to simultaneously monitor the condition of multiple patients. Accordingly, room for improvement exists.

Attempts have been made to produce wearable devices that can be used for patient monitoring. For example, one commercially available device purports to provide continuous non-invasive blood pressure monitoring using a pulse arrival time method, where optical signals from a thumb-mounted sensor are combined with ECG sensor data to provide a blood pressure estimate. The system includes a wrist-mounted transceiver to which the ECG and optical sensor are attached. Thus, the system has leads trailing over the entire upper torso of a patient, other than one arm. Further, in order to calibrate the measurements, an arm-cuff must be periodically placed about the patient's arm and coupled to the transceiver. Even with all the sensors, leads, and calibration, some medical professionals and researchers have expressed concerns over the accuracy of determining blood pressure based on pulse arrival time, as opposed to more conventional approaches such as pulse transit time.

Having a complex form factor and accuracy that may be questioned by some practitioners may limit the adoption and use cases for a wearable diagnostic device. Even in situations where it is not completely infeasible to use such devices, issues regarding accuracy and form factor can increase the associated costs. For example, additional costs, as well as patient inconvenience, are incurred if a device has to be periodically calibrated by placing a blood pressure cuff-like device about the patient's arm. Moreover, in certain use cases, such as in mass injury situations, such as natural disasters, sufficient manpower may not exist to either attach cumbersome devices to patients or to periodically calibrate the devices.

Similarly, it may be beneficial to monitor individuals who are not currently injured, but whose jobs may place them at risk of harm. For example, monitoring devices could be placed on military personnel or first responders such that any negative change in their physical condition can be rapidly determined and remedial action taken. However, if it is necessary to have sensors trailing all over the individual's body, or to periodically calibrate a device, such use cases may be impractical. For example a fire fighter, or solider may not be able to perform required tasks while having a lead running down their arm, or having a bulky transceiver attached to their wrist.

Disclosed technologies can provide various advantages. In one aspect, the present disclosure provides techniques for estimating (or determining) blood pressure, or other physiological measurements, such as shock index (the ratio a patient's heart rate divided by their systolic blood pressure), using a reduced number of sensors, sensors located in fewer body regions (including a single region), and, in some cases, a single sensor, such as a sensor providing acoustic data (e.g., phonocardiographic) or ECG data. The use of such techniques can provide a wearable device that is cheaper, less cumbersome for an individual to wear, easier to put on and take off, and more durable. Further, at least in some implementations, the measurements can be sufficiently accurate that periodic calibration is not required, or can be accomplished without attaching additional sensors to the patient.

The present disclosure also provides a software platform that can display patient diagnostic information to users in an easily understandable manner, which can expedite providing the correct treatment to a patient, thus improving medical outcomes. The displays can also facilitate a user monitoring multiple individuals simultaneously, which can allow a greater number of individuals to be serviced by a smaller number of medical professionals.

Example 2

Diagnostic System

FIG. 1 illustrates an example diagnostic system 100 according to a disclosed embodiment. The diagnostic system 100 can include a monitoring device 110 and a provider device 150. The monitoring device 110 is configured to be mounted to an individual 112, such as a patient, military personnel, first responder, or other individual whose vital signs are to be monitored. The monitoring device 110 includes a housing 114 having a front surface and a rear surface.

The rear surface is typically configured to be placed against a body surface of the patient 112, such as the patient's arm or chest. The rear surface can be covered with an adhesive material to secure the monitoring device 110 to the patient 112. Thus, the monitoring device 110 can be configured as a "sticker" that can be easily placed on the patient 112. In other aspects, the monitoring device 110 can be mounted on the patient 112 in another manner. For example, the device 110 can be secured to a band (not shown) that can extend around part of the body of the patient 112, including compressing the device 110 against the patient's body to facilitate obtaining diagnostic information.

In some cases, an outer surface of the housing 114 can be fitted with one or more sensors that can obtain diagnostic information from the patient. For example, the rear surface of the housing 114 can include a temperature sensor, such as a sensor lead or a temperature sensitive panel, which can record a patient's body temperature. The rear surface can include additional sensors or diagnostic components, such as lights and optical sensors for oximetry measurements. Additional sensors can include acoustic sensors 116, such as to measure sounds associated with heart function, including systole and diastole. Additional sensors that can be included in the monitoring device 110 include ambient temperature sensors, accelerometers, magnetometers, gyroscopes, positional sensors (e.g., global navigation satellite system or sensors that can provide location via triangulation using signals from sources such as wireless access points and Bluetooth devices), and electrical sensors, including sensors for use in measuring biopotential, including for heart rate monitoring.

As shown in FIG. 1, the monitoring device 110 can include an ECG sensor, including a lead 118. As described, ECG data can be used for a variety of purposes, including continuous, non-invasive blood pressure monitoring. More particularly, disclosed technologies provide for such blood pressure monitoring without requiring an additional sensor, such as optical sensor. As shown, the ECG sensor 118 includes a single lead, placed approximately proximate the lower portion of the heart (although other placements are possible). In another implementation, a 3-lead ECG can be used, with a lead 118 placed under the right clavicle near the right shoulder, a lead placed under the left clavicle near the left shoulder, and a lead placed on the left side of the individual below the pectoral muscles at the lower edge of the rib cage. However, it should be appreciated that in other aspects a different number of ECG leads can be used or the leads placed in other locations.

FIG. 1 also illustrates a wireless oximeter 120 coupled to a patient's finger. The wireless oximeter 120 can facilitate obtaining oximetry measurements while avoiding additional wires. However, clip-style wired oximeters can be used, if desired. Or, an oximeter can be placed on another part of the body, including being incorporated in, or proximate to, the housing 114. In yet further cases, an oximeter can be omitted.

Sensors included in the monitoring devices 110 can be used to measure or calculate a variety of physiological indicators. Some of the indicators can be obtained directly from the sensor data, such as an ambient temperature or a patient's body temperature. Other indicators can be calculated using data received from such sensors. For example, shock index can be calculated using blood pressure and heart rate.

The monitoring device 110 can incorporate any suitable sensor for obtaining desired information. A variety of suitable sensors are available from Maxim Integrated Inc. of San Jose, Calif., including the MAXREFDES100# HEALTH SENSOR PLATFORM, which includes functionality for pulse oximetry, obtaining ECG data, heart rate determination, body temperature measurement, barometric pressure sensing, and positional sensing using accelerometers and a gyroscope.

The provider device 150 is typically configured to be carried by a medical personnel 152 and includes a display screen 154, such as a capacitive touch screen. As opposed to having a display 154 located on the patient 112, sending data to the provider device 150 carried by medical personal 152 can be advantageous, as the medical personnel may monitor the status of a patient remotely, or without having to locate a patient-mounted display, and may more easily monitor the status of multiple individuals.

In some cases, the provider device 150 can be a special purpose computing device. However, in other aspects, the provider device 150 can be a smart phone or similar device (e.g., a tablet or PDA form factor) that can run software (e.g., an app) that receives data directly or indirectly from the monitoring device 110. The display screen 154 can provide the medical personnel 152 with various information regarding the patient 112. The information on the display screen 154 can include information provided by, or calculated from, the monitoring device 110. In some aspects, the display screen 154 can provide additional information, such as identifying information for the patient 112 (e.g., by accessing medical records for the patient or other patient information).

Figure 2:
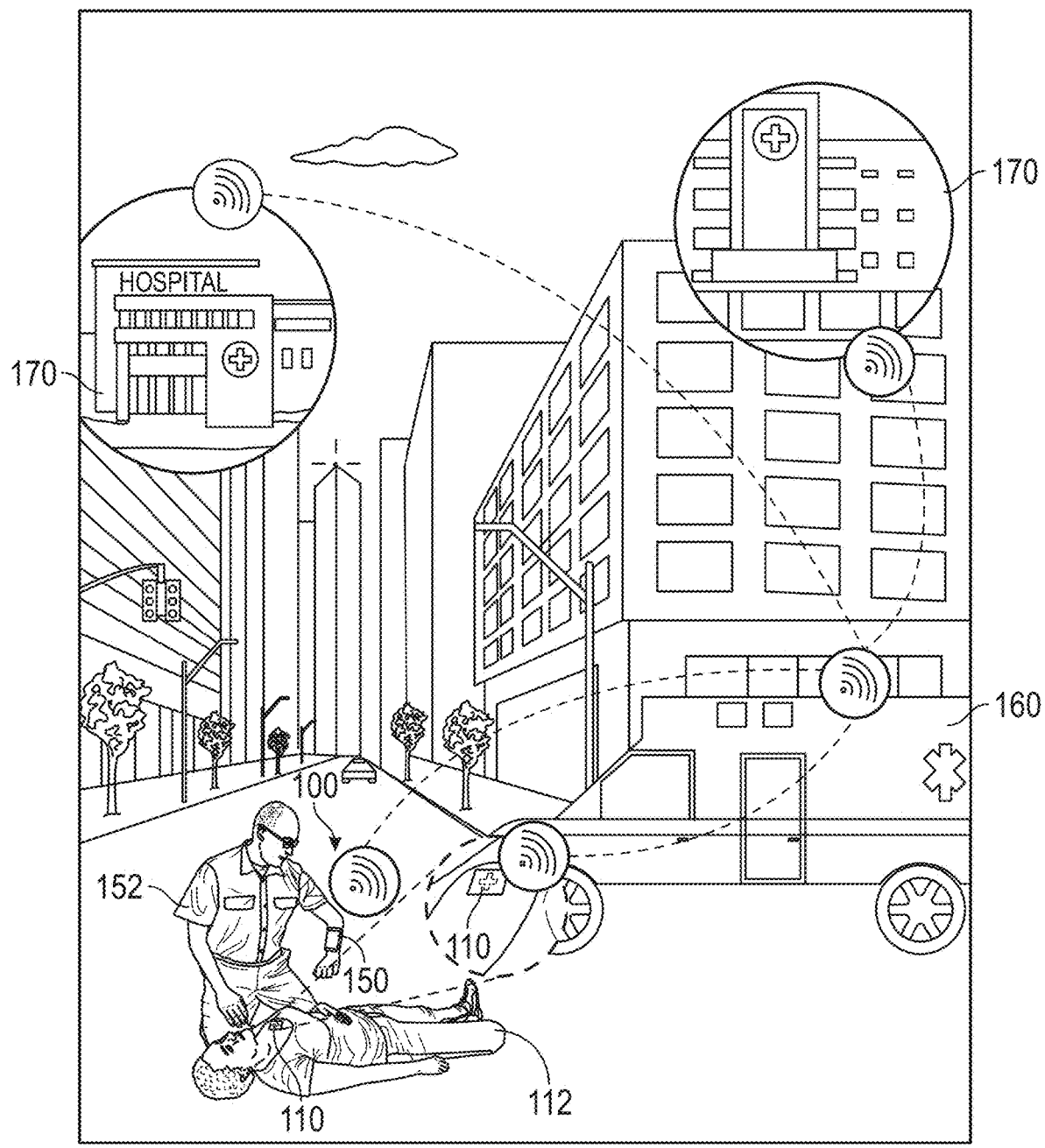
FIG. 2 is a depiction of an example scenario in which one or both of a patient monitoring device and a provider device can be in communication with other computing systems.

FIG. 2 illustrates the diagnostic system 100 in a use case scenario. The medical professional 152 can attach the monitoring device 110 to the patient 112, which can then sync with the provider device 150, or the medical professional can place the provider device in communication with a monitoring device that has already been placed on the patient. For example, in some cases, a first responder or other individual may be fitted with a monitoring device 110 so that the individual can be monitored to determine if a health issue arises, and to expedite and improve treatment.

The monitoring device 110 may communicate with the provider device 150 directly or indirectly. For example, the monitoring device 110 and the provider device 150 may communicate via Bluetooth, nearfield communications, cellular communications, Wi-Fi, or another suitable protocol. Typically, the monitoring device 110 and the provider device 150 are capable of wireless communication. However, the monitoring device 110 and the provider device 150 can be physically connectable, if desired. For example, the monitoring device 110 and the provider device 150 can be coupled via a USB cable. Having multiple, potentially redundant, communication methods available may be useful in the event that wireless communications are not available, in the event of component failure, or for other reasons.

The monitoring device 110 or the provider device 150 may be in communication with other devices, which other devices may also allow for indirect communication between the monitoring device and the provider device. For example, the monitoring device 110 or the provider device 150 may communicate with devices located in an emergency vehicle 160 (e.g., an ambulance, fire engine, helicopter, military transport, etc.). For example, the emergency vehicle 160 may have additional diagnostic equipment or computing systems that can access data from the monitoring device 110, and can serve to analyze or augment the data, or to provide an additional, and potentially more convenient, display to a medical professional.

Similarly, one or more of the monitoring device 110, the provider device 150, or the emergency vehicle 160 may communicate with computing systems located in one or more medical facilities 170, such as hospitals, clinics, diagnostic centers, and the like. In at least some cases, a central server may serve to collect and distribute information from the monitoring device 110, and optionally information from the provider device 150, the emergency vehicle 160, or the medical facilities 170. For instance, a medical professional may enter treatment information, such as interventions or medications administered, and this information may be associated with the patient 112. Collecting resources at a centralized location can assist in continuing treatment from a field location, to an emergency vehicle 160, and between treatment facilities 170. In addition, the centralized location may provide access to real-time as well as historical diagnostic patient information. For example, the historical information may be used to provide trend information and summary information to a medical professional (e.g., a graph of values for a particular vital sign over time).

Example 3

Example Blood Pressure Measurement

As discussed above, typical methods of estimating blood pressure on a continuous basis involve the use of multiple sensors, including sensors that are typically spread out across a patient's body. Disclosed monitoring devices, and techniques, can allow for continuous blood pressure monitoring, as well as monitoring and determining other vital signs, using a lower number of sensors or types of data. For example, blood pressure can be estimated or determined using only ECG data, or only acoustic data.

In at least some examples, a monitoring device, such as the monitoring device 110 of FIG. 1 can include multiple sensors. However, only one type of sensor, or sensor data, is necessary for continuously estimating or determining blood pressure. Other sensors may be included to measure other vital signs, or used to measure quantities from which other vital signs can be calculated. In at least some aspects, all of the sensors of a disclosed monitoring device are confined to a single location on a patient's body, such as the patient's chest. However, in some implementations, a disclosed monitoring device can include sensors at multiple locations on a patient's chest, such as for obtaining ECG data.

Figure 3:
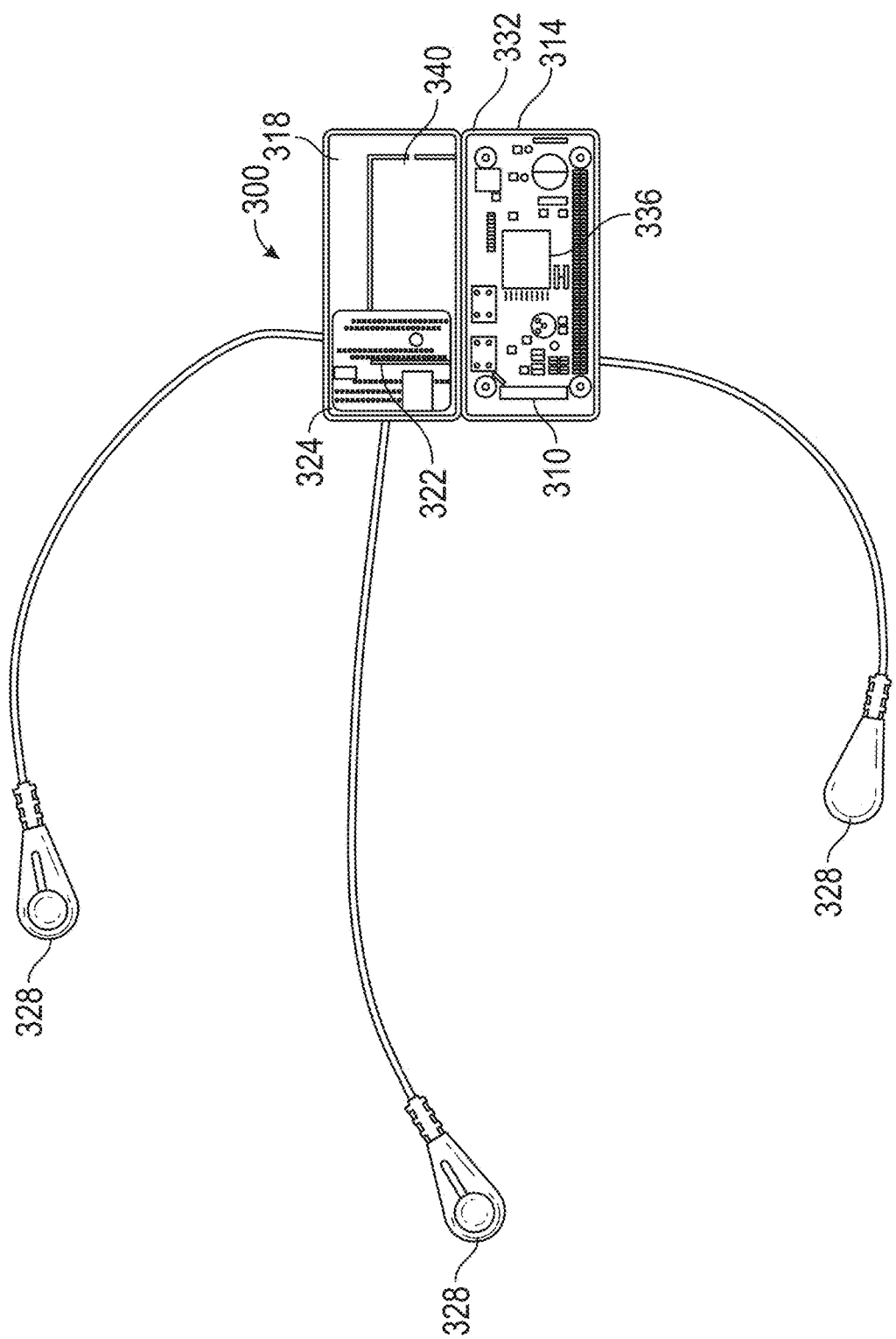
FIG. 3 is a perspective view of an embodiment of a patient monitoring device of the present disclosure.

FIG. 3 illustrates an example monitoring device 300, which can be the monitoring device 110 of FIG. 1. The monitoring device 300 can include a housing 310. The housing 310 can have a front member 314 hingeably connected to a rear member 318. The front member 314 can be rotated with respect to the rear member 318 to allow access to the interior of the monitoring unit 300. In other embodiments, the monitoring device 300 has a unitary housing 310 (e.g., a single piece of plastic molded about internal components of the device) or is formed from multiple components coupled together other than in a hingeable manner (including having the front member 314 engage the rear member 318 in a snap-fit manner).

The device 300 can include a recessed compartment 324 for receiving a sensor unit 322. In a particular example, the sensor unit 322 can be the MAXREFDES100 of Maxim Integrated Inc. of San Jose, Calif. The sensor unit 322 can be coupled to three ECG leads 328. Alternatively, the sensor unit 322 can include an acoustic sensor and/or other type of sensor.

The monitoring device 300 can include a recessed compartment 332 for receiving a processing unit 336. The processing unit 336 can be a single-board computer, such as a RASPBERRY PI (for example, the RASPBERRY PI ZERO) or an ARDUINO unit. The processing unit 336 can collect data from the sensor unit 322, perform calculations, and communicate data, such as to the provider device 150 of FIG. 1. For example, the processing unit 336 can monitor sensor data and generate an alert when particular criteria are met. Such criteria can include a measured blood pressure, or calculated shock index, satisfying a threshold (e.g., exceeding or failing to exceed a certain value). The alert can be sent wirelessly, such as using Bluetooth or Wi-Fi capabilities of the sensor unit 322 or the processing unit 336.

Although a processing unit 336 and a sensor unit 322 are shown in FIG. 3, other configurations can be used. For example, in some aspects, the processing unit 336 can be omitted. Some applications may not require monitoring or calculations to be performed within the monitoring device 300, and so data may be stored on the monitoring device or may be transmitted and processed on a device other than the monitoring device. In particular, the sensor unit 322 can include wireless functionality, such as Wi-Fi or Bluetooth. In yet further aspects, the processing unit 336 and the sensor unit 322 can be integrated into a single component.

The monitoring device 300 can include a recessed compartment 340 for receiving a power supply (not shown). The power supply can be a battery, such as lithium-polymer battery.

Example 4

Example Cardiac Feature Sets

Sensor data, such as ECG or acoustic signals, can be used to measure a variety of features related to heart function. For example, the sensor data can convey information regarding sinus rhythm, including the height of the R-wave (electrical stimulus as it passes through the main portion of the ventricular walls), the height of the T-wave (resulting from ventricular repolarization), and the distance between the R-wave and the T-wave. Acoustic information can include the onset, completion, and duration of atrial or ventricular contraction and the onset, completion, and duration of atrial or ventricular relaxation.

ECG and acoustic data can be used alone, or in combination, for various diagnostic purposes, including estimating blood pressure. ECG and acoustic data may be used to construct feature sets, where a feature set can be used alone or in combination with other feature sets (or other data) for diagnostic purposes. Example feature sets include:

- Height of R and T waves;
- Distance (e.g., time) between R and T waves;
- Distance between peak R wave and end of ventricular contraction (including as indicated by acoustic data, such as the "lub" sound associated with mitral valve closure);
- Length of ventricular contraction (including as indicated by acoustic data, such as the length and quality of the "lub" sound);
- Distance between peak T wave and end of ventricular contraction (including as indicated by acoustic data, such as the "dub" sound associated with atrial valve closure);
- Length of ventricular/atrial relaxation (including as indicated by acoustic data, such as the length and quality of the "dub" sound); and
- Distance between end of ventricular contraction and onset of ventricular relaxation (including as indicated using acoustic data, such as the distance between the end of the "lub" sound and the onset of the "dub" sound).

The feature set(s) used, and other considerations, can affect what sensors are included in a monitoring device. For example, one or more acoustic sensors, and in some cases between four and five acoustic sensors, can be placed on a subject's chest, such as in a linear array across the chest. In a particular implementation, the acoustic sensors can be electret microphones. A linear array of microphone sensors can be used to accurately determine ventricular contractions, ventricular/atrial relaxations, determine the time between contraction and relaxation, as well as detect heart irregularities including murmurs and arrhythmias.

The three-lead ECG discussed above can be used, or another configuration can be used, including a single lead that is placed in the vicinity of the acoustic sensors, including along the line of the linear array. To increase sensitivity, the measured acoustic signals can be filtered, such as filtering sounds over about 500 Hz. In particular, heart sounds of interest can typically be measured in the range of about 20

Hz to about 500 Hz, or between about 100 Hz and about 500 Hz. In more specific examples, the heart sounds of interest are measured in a range of between 20 Hz and 500 Hz or between 100 Hz and 500 Hz.

Figure 4:
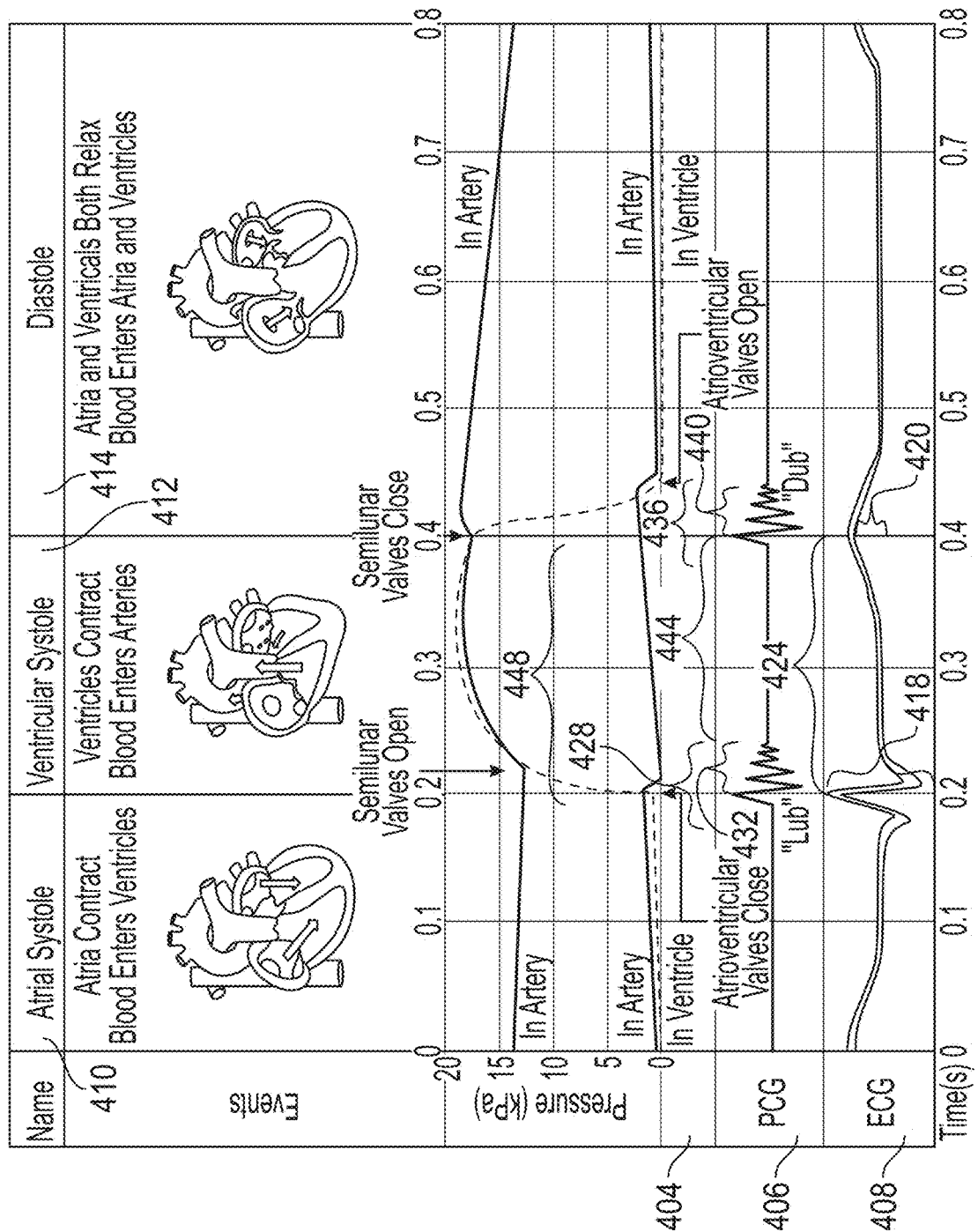
FIG. 4 is a graph illustrating relationships between blood pressure, phonocardiographic measurements, and ECG measurements, and correlations to atrial systole, ventricular systole, and atrial/ventricular diastole.

FIG. 4 illustrates graphs of pressure (kPa) 404, phonocardiographic data (amplitude) 406, and ECG data (millivolts) 408 versus seconds for periods of the cardiac cycle, including atrial systole (atrial contraction) 410, ventricular systole 412 (ventricular contraction), and diastole 414 (atrial and ventricular relaxation). FIG. 4 illustrates how maximum R wave 418 and T wave 420 heights may be extracted from the ECG data 408. FIG. 4 also illustrates how the distance 424 between the maximum R and T wave heights 418, 420 can be determined from the ECG data as the distance between the peaks of the respective waves. As can be seen, the distance 424 can represent the duration of ventricular systole 412.

FIG. 4 illustrates how the feature set of the peak 418 of the R wave and the end of ventricular contraction can be determined from the phonocardiographic data 406 and the ECG data 408, as indicated by the distance 428. Specifically, the distance 428 can be defined as the beginning or onset of the R-wave to the end of the last wave of the acoustical signal ("lub" sound) associated with ventricular contraction. Similarly, FIG. 4 illustrates how the length 432 of ventricular contraction can be determined from the phonocardiographic data 406 as the onset of the initial wave associated with ventricular contraction to the end of the final wave associated with ventricular contraction.

FIG. 4 further illustrates how the feature set of the duration 436 between the onset of the T-wave to the end of ventricular relaxation ("dub" sound) can be determined from the phonocardiographic data 406 and the ECG data 408, as the onset of the T-wave to the end of the final wave associated with ventricular/atrial relaxation in the phonocardiographic data 406. FIG. 4 illustrates how the duration 440 of the sound associated with ventricular/atrial relaxation can be determined from the beginning of the first wave and the end of the final wave of the measured acoustic signal for the ventricular/atrial relaxation. The determination of a period 444 representing the end of the "lub" sound to the beginning of the "dub" sound is illustrated in FIG. 4, where the phonocardiographic data 406 is measured between the end of the final wave associated with ventricular contraction to the onset of the first wave associated with ventricular/atrial relaxation. FIG. 4 illustrates how the duration 448 between the onset of the "lub" sound and the onset of the "dub" sound can be determined from the phonocardiographic data 406 as the onset of the first wave associated with ventricular contraction and the onset of the first wave associated with ventricular/atrial relaxation.

The above-described feature sets can be used to estimate (or determine, such as determine as an estimate) blood pressure, as well as derive other information regarding cardiac properties and health. For example, measurements of when heart valves open and close can be used to estimate blood velocity. That is, if the distance blood must travel in the heart's left atrium and left ventricle is known, then the time taken for blood to enter and exit the heart can be used to calculate blood velocity. In some cases, the distance can be estimated as the average distance blood will travel through one or more heart chambers before reaching its next destination (e.g., passing through a valve). For example, for atrial systole, the distance can be the average distance blood will travel in passing from the atria into the ventricles. For ventricular systole, the distance can be the average distance blood will travel before passing through the pulmonic valve and the aortic valve. For diastole, the distance can be the average distance blood will travel after passing through the inferior and superior vena cava and the pulmonary veins into the atria, such as from where these structures open into the atria.

With the blood velocity determined, blood pressure can be calculated in various manners. In one aspect, blood pressure can be calculated using a simplified linear force model derived from Newton's Second Law of Motion, taking into account that force is proportional to a change in velocity (e.g., the blood velocities discussed above give rise to a force, such as a force associated with ejecting blood through a heart valve, that can be used to determine blood pressure):

$$\text{Pressure} = \frac{F*4}{A_a} \tag{1}$$

In Equation 1, $A_a$ is the area of the aortic valve (~1.5 cm), and F represents the atrial ejection force based on the time, t, it takes to empty a fixed volume of blood from the left ventricle ($V_v$) through the area of the heart's aortic valve ($A_a$):

$$F = \rho * A_a * \left(\frac{V_v}{t*A_a}\right)^2 \tag{2}$$

In Equation 2, p is blood density (~1.06 g/cm$^3$), V the stroke volume (~75 cm$^3$) and the area of the aortic valve is approximately 1-2 cm$^2$.

As an example of how Equation 1 can be used to calculate blood pressure, a value of 1.5 cm can be used for the aortic diameter, the stroke volume is assumed to be 75 cm$^3$, and the blood density is taken as 1.06 g/cm3. Assuming an average R-T time is measured on the ECG as 0.240 seconds, a systolic blood pressure of 184 kdynes/cm$^2$ is determined, or equivalently, 138 mmHg.

Using the acoustic features described, the estimate can be adjusted. As an example, the murmur of mitral regurgitation creates turbulence that can be detected in the acoustic data following the classic "lub" sound of the mitral and tricuspid valves. This turbulence is audibly heard after valve closure as a hissing, or "whooshing" noise. The amplitude of this hissing in comparison to the "lub" sound is an indicator of the degree of regurgitation that corresponds to blood leaking back into the left atrium during systole. These regurgitations effectively reduce the total stroke volume that the left ventricle is able to pump into the aorta. By comparing the amplitude of these regurgitations to the "lub" of mitral valve closure, the volume of blood lost during the regurgitation process can be estimated and accounted for by reducing the total stroke volume used in the blood pressure estimate, providing more accurate results. That is, in the above example, for patients having the same R-T time, the estimated blood pressure may be different based on the acoustic features measured for each patient.

Continuing the example above, assume that a murmur in the mitral valve is detected and that the amplitude of its signal (i.e., the strength of the hissing or whooshing sound of blood turbulence) is ~$\frac{1}{10}$ the size of the "lub" amplitude. This ratio can be classified as mild regurgitation and can correspond to a loss of ~5 cm$^3$ in stroke volume. The estimate for blood pressure can be adjusted by lowering the stroke volume accordingly. Assuming that all other parameters remain the same, the estimate for blood pressure is now ~120 mmHG. Stroke volume can also be adjusted based on other factors, such as age, race, gender, height, weight, or medical history. Demographic data for a patient can be obtained and compared with a library to determine a stroke volume correction factor to be used, including a determination of not to apply a correction factor.

In some cases, an equation can be used to correlate the amplitude (or, in some cases, duration, or a combination of duration and amplitude) acoustic signals corresponding to regurgitation or similar physiological features with a change (typically a decrease) in stroke volume. In other cases, an acoustic signal corresponding to regurgitation can be analyzed (including by comparing the amplitude with the "lub" amplitude) and classified into an interval, where an interval is associated with a defined correction factor. For instance, intervals can be defined on a scale of 1 to 6, with 1 being "no adjustment" and 6 being a highest amount of adjustment. In some cases, a correction factor can be determined once for a particular patient and stored for further use with data obtained from the patient, which can eliminate the need to continually determine a stroke volume correction for the patient.

As another example of how blood pressure can be calculated using one of the above-described features, the Hagen-Poiseuille model can be modified as shown in Equation 3 to determine systolic blood pressure (in mm Hg) using the distance between the R and T waves:

$$\text{Pressure} = \frac{256 L \eta SV}{\frac{3}{4}\pi r^4 T_{Fill}} \quad (3)$$

where η is blood viscosity (in mmHg), L is the length of the aorta (m), SV is the stroke volume (m$^3$), r is the aortic radius (m), and T$_{Fill}$ is the time taken to fill the arteries with blood (empty the chambers of the heart), as read from ECG data or from phonocardiographic measurements (e.g., time between mitral valve closure, end of "lub", and atrial valve closure, end of "dub").

As an example of how Equation 3 can be used to calculate blood pressure, a value of 1.5 cm can be used for the aortic diameter, the stroke volume is assumed to be 9.5×10$^{-5}$ m$^3$, the blood viscosity is taken as 1.28×10$^{-4}$ mmHg, and a value of 7.5 cm is used for the length of the aorta. Using an example fill time of 0.200 seconds, such as determined by ECG or phonocardiographic measurements, a systolic blood pressure of 156 mm Hg is determined. The stroke volume can be adjusted as described for Equation 2 using acoustic data to determine an amount or degree of regurgitation or other condition that might result in a lower stroke volume.

Values corresponding to physiological features, such the size and volume of a heart chamber, the size of blood vessels, the distance blood travels after leaving the ventricles etc. can be an average value, a value selected based on demographic information, values based on individual assessment, or values adjusted based on empirical data. For example, the average aortic length and diameter of a sample group may be used to provide a reasonable approximation of blood pressure. Or, average values can be selected from a sample group of which the patient is a member, such as sample group based on gender, race, height, weight, age, or combinations thereof. A software implementation of a blood pressure monitoring method can include a repository that stores values to be used with demographic information for a particular patient.

In at least some cases, until such demographic information is known, an average value can be used. Or, the method can include updating a patient profile as demographic information is obtained. For example, in an emergency situation, only information such as a patient's gender may initially be known. That information can be used to provide values that should more accurately reflect blood pressure than values for a generic human. However, additional information can be included as available, or estimated values can be initially used and revised as more accurate information becomes available. For instance, a user interface of a provider device, such as the provider device 150, can include boxes where an estimated weight or height (or other parameter) can be entered, or selected from a list or dropdown menu of possible values (e.g., weights in 20 pound increments). As additional, or more accurate information, such as age, race, height, and weight, becomes available, it can be entered into software and used to increase the accuracy of future calculations (and, in some cases, can be applied to adjust previously determined blood pressures). In some cases, as a patient is transitioned between medical providers, additional information regarding the patient can be entered into software to obtain more accurate blood pressure values, and such information that can be obtained to increase accuracy can be indicated to a subsequent medical provider in the form of a "to do," task, or action item.

Example 5

Example User Interface

Figure 5:
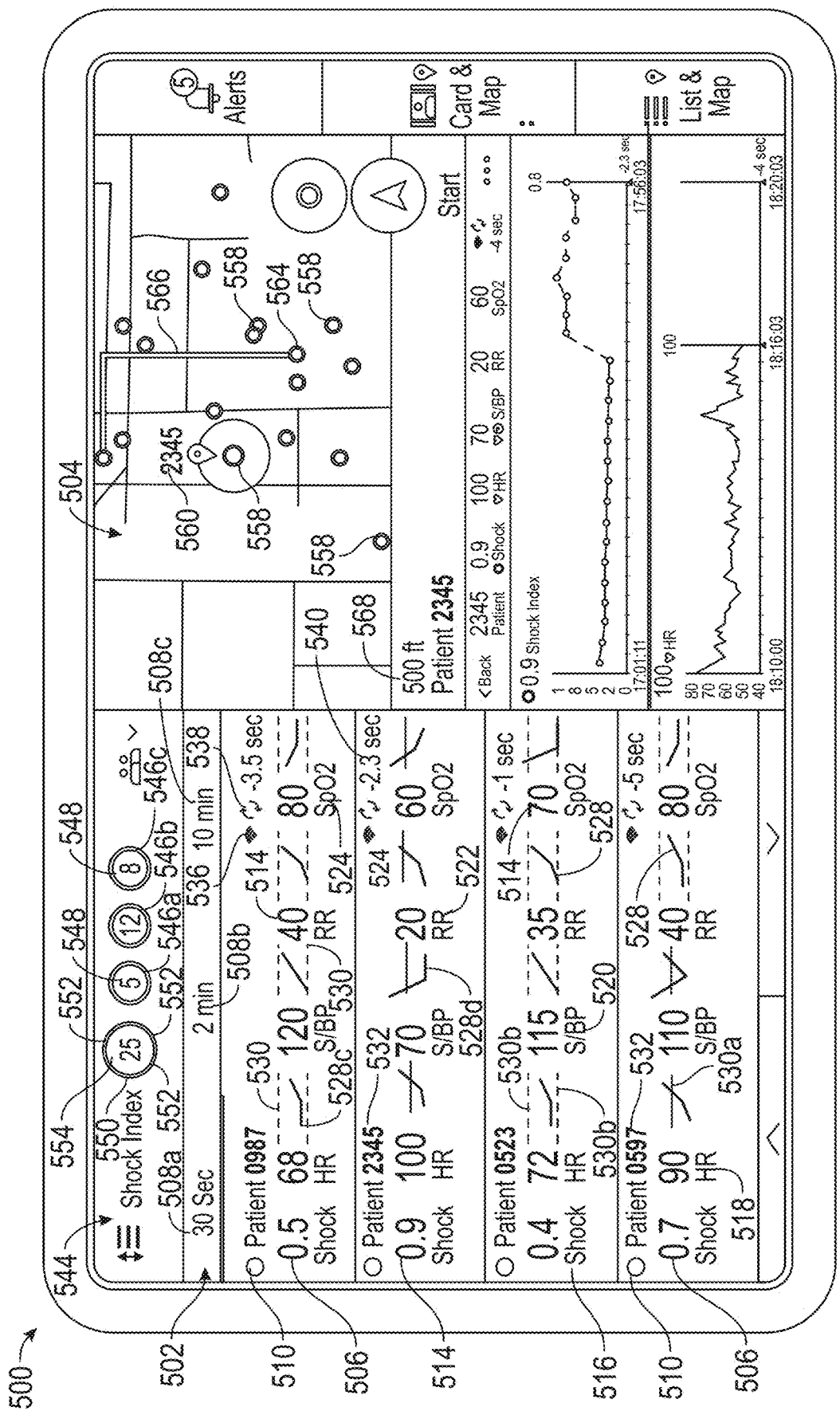
FIG. 5 is a diagram illustrating an example user interface screen that can provide diagnostic and geospatial information for a plurality of monitored individuals.

FIG. 5 illustrates an example user interface screen 500 that can be used to convey patient monitoring information to a user. For example, the user interface screen 500 can be displayed on the monitoring device 110 or the provider device 150 of FIG. 1, or on another computing device, such as a computing device located in an emergency vehicle, in a clinic or hospital, or on a device (such as a tablet or smart phone) carried by medical personnel.

The user interface screen 500 includes a patient diagnostic information section 502 and a geospatial, or map, section 504. The patient diagnostic information section 502 includes a plurality of rows 506, with each row including diagnostic information for a particular patient (or other monitored individual). The rows 506 include diagnostic information for a particular time period. A user may select from various time periods by selecting (e.g., by touching, swiping, clicking, or other type of interaction) a time period indicator 508. As shown, the screen 500 displays a time period indicator 508a for a most recent thirty second time period, a time period indicator 508b for a most recent two minute time period, and a time period indicator 508c for a most recent ten minute time period. Different time periods may be used, and a different number of time periods may be available. In some cases, only a single time period is provided, or the screen 500 can present real-time data.

Each row 506 can include a patient status indicator 510. The patient status indicator 510 can be colored to represent a patient status, such as green (indicating that the patient is stable or healthy), yellow (indicating that the patient's condition may be worsening or should be monitored more closely for changes), or red (indicating that the patient's condition is worsening and that the patient may need urgent attention). Other colors can be used for the status indicator 510, or the patient status can be indicated in another manner, such as emoticons.

The patient status indicator 510 can be based on one vital sign or a combination of vital signs, or a measure calculated from one or more vital signs. In a particular example, the patient status indicator 510 can be correlated with shock index, which can be defined as the ratio of heart rate to systolic blood pressure. Although various thresholds or intervals can be defined, in one example, a shock index of less than 0.6 indicates no shock (and may be correlated with a green patient status indicator 510), a shock index of 0.6 to less than 1.0 indicates mild shock (and can be correlated with a yellow patient status indicator), and a shock index of 1.0 or greater indicates moderate shock or higher (and can be correlated with a red patient status indicator). If desired, additional intervals can be defined, such as separating a shock index of 1.0 or higher into a moderate shock range of 1.0 to less than 1.4 and a severe shock range of 1.4 or greater. In a further, particular, example, the shock index ranges are defined as between 0.9 and less than 1.1, between 1.1 and less than 1.3, and greater than 1.3.

Each row 506 can present diagnostic information, such as vital sign readings from sensors or calculated values (such as shock index) for a patient. The diagnostic information can includes values 514 for shock 516, heart rate 518, systolic blood pressure 520, respiration rate 522, and peripheral capillary oxygen saturation 524. If desired more, fewer, or different types of diagnostic information can be provided. In some cases, the diagnostic information (516, 518, 520, 522, 524) can represent a current (or most recent) value that was received from a sensor on the patient, or calculated using sensor data. In other cases, the diagnostic information (516, 518, 520, 522, 524) can represent an average value over a time period, such as the time period associated with the time period indicator 508.

One or more values of the diagnostic information 516, 518, 520, 522, 524) can be displayed in association with a graphical representation 528 of how the values have been trending, such as over the time period associated with the time period indicator 508 or compared with one or more earlier time periods. The graphical representation 528 can be represented as a trend or spark line. In some cases, rather than indicating a change or trend, one or more of the graphical representations 528 can be a graphical depiction of sensor measurements, or quantities calculated from sensor measurements, such as a graph of heart rate or systolic blood pressure.

The graphical representations 528 can be implemented in different manners. For example, one or more of the graphical representations 528 can generated directly from sensor data—such as being a plot of actual data points from sensor measurements or quantities calculated therefrom. In another implementation, the graphical representations 528 can be selected from a set of pre-rendered icons, where an icon is selected that best matches a data trend for particular diagnostic information.

The graphical representation 528 can include one or more indicators 530, which can be used to indicate a normal value or normal range for a particular diagnostic. For example, indicator 530*a* is in the form of a line representing an average heart rate value. Indicators 530*b* are in the form of a pair of lines representing upper and lower bounds of a normal range for heart rate.

Each row 506 can include one or more patient identifiers 532. In some cases, a patient identifier 532 can be a numerical value assigned to a patient. However, other patient identifiers, including patient names, can be used. As will be further described, in at least some aspects of the disclosed technologies, a user may be able to obtain more information about a particular patient by selecting (e.g., clicking, touching, swiping) on the appropriate row 506.

Each row 506 can include information regarding the status of a monitoring device associated with the corresponding patient. For example, an icon 536 can indicate if and how the monitoring device is connected to a device associated with the screen 500, or an intermediate computing device (e.g., a server). The icon 536 can indicate whether the monitoring device is connected via Wi-Fi, cellular network (e.g., LTE), Bluetooth, or another method, and, optionally, an indication of connection quality.

A refresh icon 538 can indicate whether information from a monitoring device is being refreshed or synchronized. In some cases, the refresh icon 538 can be selected (e.g., clicked or pressed) to cause a refresh to be initiated. A refresh value 540 can be provided to indicate the time a last refresh occurred. In some cases one or both of the refresh icon 538 and refresh value 540 can be omitted. For example, refresh can be set to occur at particular intervals, which, in some cases, can be user adjustable, or can be configured based on patient status (e.g., refresh occurs more quickly for patient's having a "yellow" or "red" status).

The diagnostic information section 502 can include a status summary section 544, which can summarize the status of a plurality of patients associated with a provider device 150 or another computing device. The status summary section 544 is shown as providing a summary of shock index information for the patients. Circular icons 546 are provided for low 546*a*, medium 546*b*, and high 546*c* shock levels. A number 548 of patients in a given category can be provided inside of the respective circular icon. The icons 546 can be color coded to help convey category information, and the coloring can correspond to the patient status identifiers 510. A circular summary icon 550 can visually depict the status of all monitored patients, including colored segments 552 representing the different shock categories, where the size of the segment is correlated with the number of patients in the category, and the color of the segment can correspond with patient status. The total number 554 of monitored patients can be placed within the circular icon 550.

The map section 504 can display navigational information to a user, which may be in the form of a "map" view (e.g., a computer generated map with graphical representations of streets, buildings, etc.) or a "satellite" view (e.g., a display of satellite images, which may be augmented with computer-generated features, such as highlighting roads or particular navigational routes). Patient icons 558 can be displayed on the map section 504, proximate the corresponding geophysical location of the patient.

In some cases, the patient icons 558 can be updated in real time based on sensors associated with the patient, such as sensors included in a monitoring device. Suitable sensors include GNSS sensors, although other means of location, including triangulation using wireless access points, can be used. In other cases the patient icons 558 can be based on other data, including having a user (such as a dispatcher) manually enter a patient's location, which can then be updated as additional information is received (e.g., the patient is known to have been moved to a hospital). Combinations of the above approaches can be used. If a monitoring device does not include positional sensors, an initial patient position can be set manually. If the patient is located in an emergency vehicle that does have positional location, the patient's location can be set to the vehicle's location and updated in real time.

The patient icons 558 can include additional information regarding a patient (or other monitored individuals) associated with a respective icon. For example, the patient icons 558 can be colored to display patient status information, which can be correlated with the patient status indicators 510. In this manner, a user may quickly identity patients in an area, and obtain an indication of their health status. Such information can be useful in activities such as dispatching and triage.

A user may be able to obtain more information by selecting (e.g., pressing or clicking) on a patient icon 558. For example, clicking on a patient icon 558 may cause a patient identifier 560 to be displayed, which can be the same as the patient identifier 532. In some implementations, selecting a patient icon 558 can cause the diagnostic information section 502 to change to provide more detailed health information for the selected patient.

The map section 504 can display an indicator 564 for a user of a display providing the screen 500. In this way, the user may assess how far they are from a patient, and how to get to the patient's location. The map section 504 can include navigational features, such as providing route information for reaching a patient, including a route display 566, a route summary (e.g., turn-by-turn information) or providing real time navigational assistance. The map section 504 can also display a distance 568 between the user and a selected patient. The map section 504 can be configured to display other types of information, including locations of medical personnel, medical vehicles, medical facilities, and the like.

Figure 6:
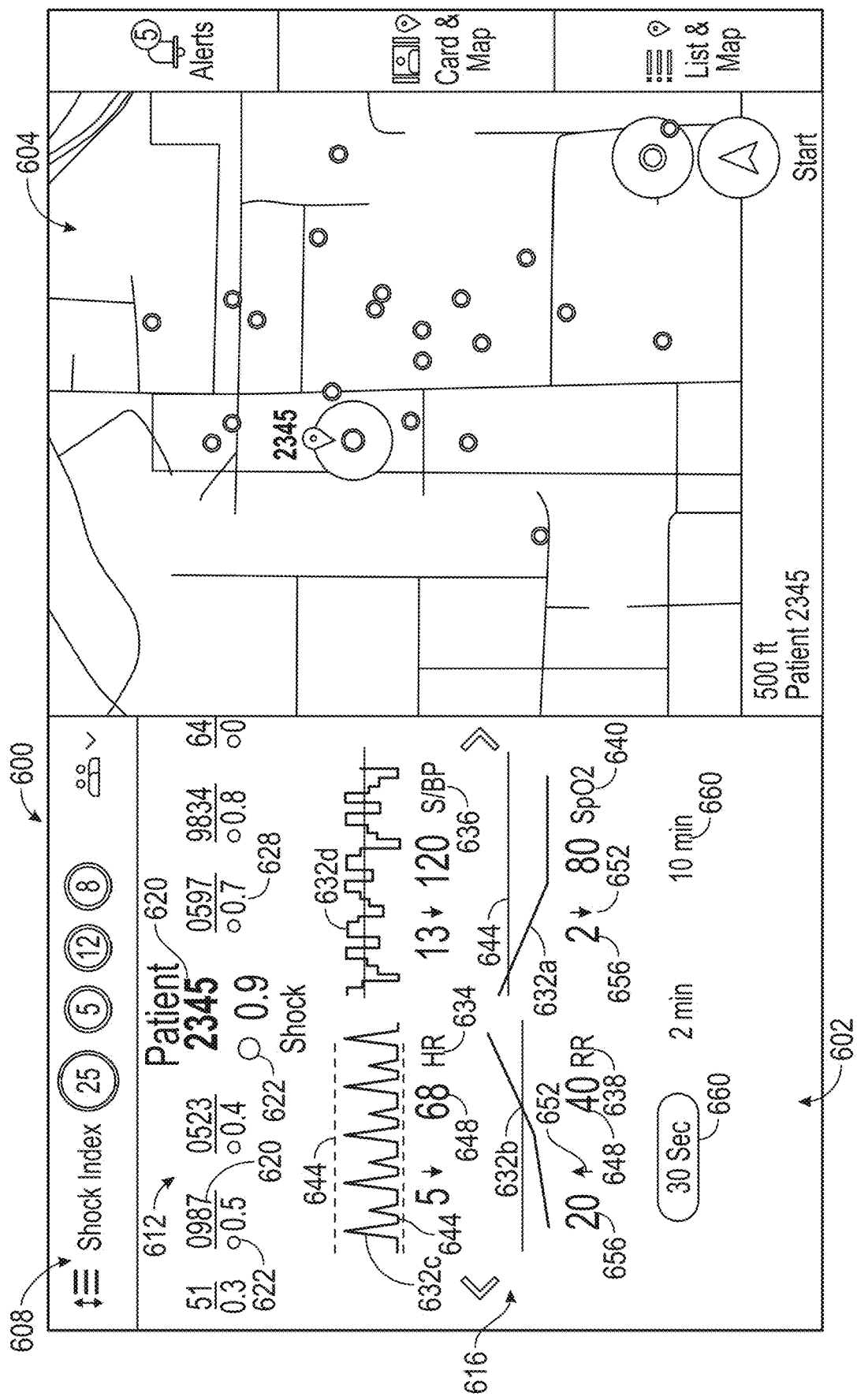
FIG. 6 is a diagram illustrating an example user interface screen that can provide more detailed diagnostic information for a particular monitored individual, along with geospatial information for a plurality of monitored individuals.

FIG. 6 illustrates an example user interface screen 600 which can provide a user with additional detail regarding a patient, such as a patient selected through the screen 500 (such as by selecting a row 506 or a patient indicator 558). The screen 600 can include a patient information section 602 and a geospatial section 604. The geospatial section 604 can be at least generally similar to the geospatial section 504 of FIG. 5 and so will not be further described.

The patient information section 602 can include a status summary section 608, which can be at least generally similar to the status summary section 544 of FIG. 5. A patient selection portion segment 612 of the screen 600 can allow a user to switch between patients whose diagnostic information will be provided in a diagnostic section 616. For example, the user may swipe, touch, or click in the segment 612 to select a different patient.

The patient selection portion 612 can include patient identifiers 620 (which can be similar to the patient identifiers 532) for each patient, as well as a patient status indicator icon 622 (which can be similar to the patient status indicators 510) and, optionally, a diagnostic value 628. The diagnostic value 628 can be the current shock index associated with the particular patient. The diagnostic section 616 can include graphical representations 632 of various diagnostic information, which, as in FIG. 5, can include heart rate 634, systolic blood pressure 636, respiration rate 638, and peripheral capillary oxygen saturation 640.

In some cases, such as graphical representations 632a, 632b, the graphical representation can be at least generally similar to the corresponding graphical representations 528 of FIG. 5. However, the graphical representations 632a, 632b can be larger than counterpart representations 528. In other cases, such as graphical representations 632c, 632d, the graphical representations of FIG. 6 can be different than the graphical representations 528. For example, graphical representation 632c can be an ECG trace, from which heart rate can be calculated. However, the graphical representation 528c for heart rate in FIG. 5 provides a summary of heart rate change, as opposed to providing sensor data. Similarly, the graphical representation 632d can present granular details of systolic blood pressure calculations (e.g., including values that actually represent clinic systolic blood pressure values), whereas the representation 528d presents only a summary of the trend of clinic values.

Other aspects of the presentation of diagnostic information 634, 636, 638, 640 can be similar to FIG. 5 including the use of indicators 644 (analogous to indicators 530) to indicate normal or average values, or a range of normal or average values. Similarly, the diagnostic information 634, 636, 638, 640 can include values 648. In addition to the values 648, the diagnostic information 634, 636, 638, 640 can include a trend indicator 652, such as an up or down arrow, indicating how the values are trending (e.g., increasing or decreasing). A change value 656 can also be displayed, indicating an amount of change, such as an amount of change compared with a previous time period or another baseline value.

The patient information section 612 can include time period indicators 660, which can be analogous to the time period indicators 508 of FIG. 5. The time period indicators 660 can allow a user to determine a time interval associated with a current information display, as well as to change to a different interval.

Figure 7:
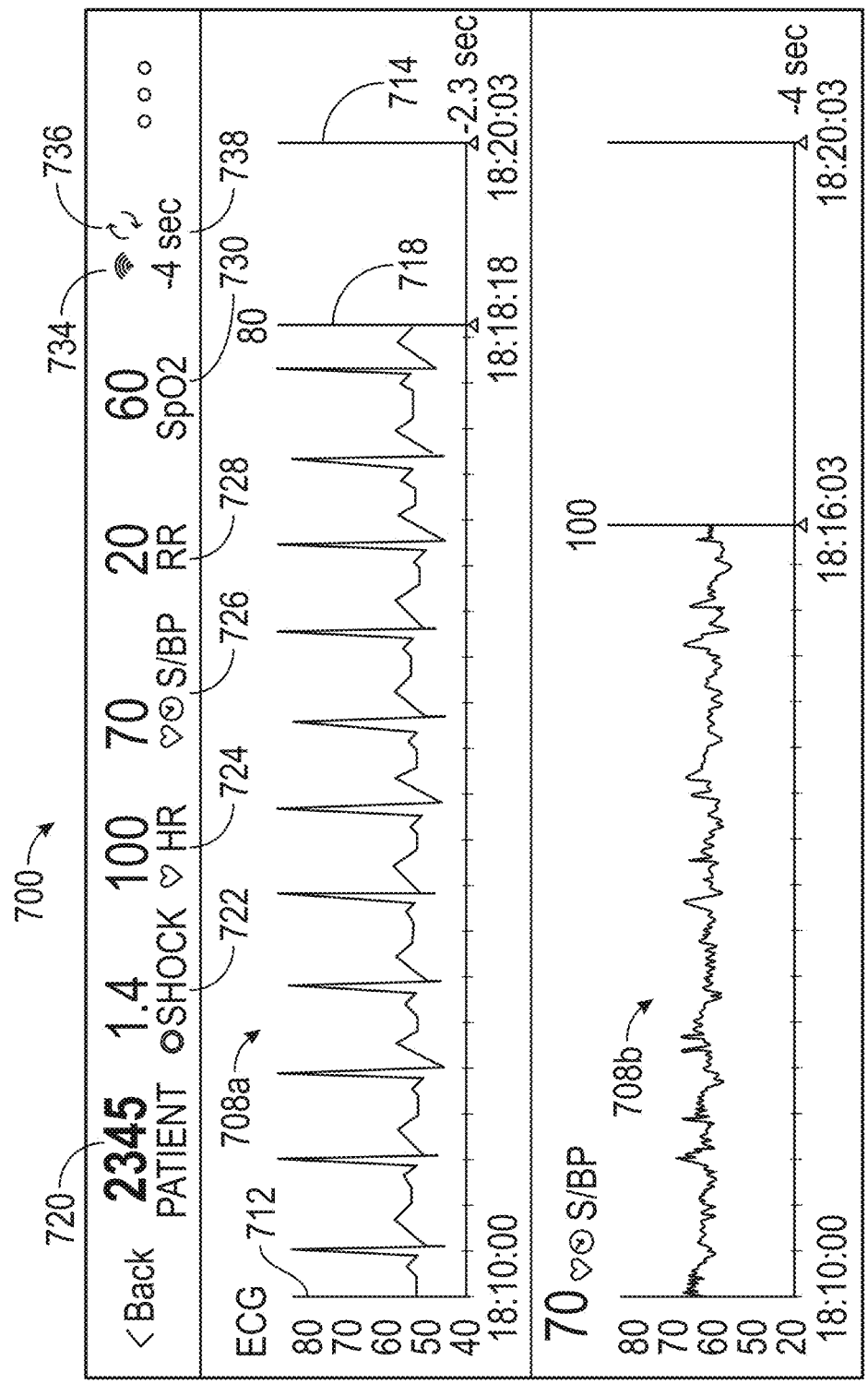
FIG. 7 is a diagram illustrating an example user interface screen that can provide detailed vital sign sensor or calculation information over a time period, including real time data.

FIG. 7 illustrates a real time sensor data screen 700. In some aspects, a user may navigate to the screen 700 by selecting an appropriate icon from the screen 500 or the screen 600. For example, the user may navigate to the screen 700 by selecting a value 514 or a value 648. The screen 700 can present sensor traces 708, such as sensor trace 708a for ECG data and sensor trace 708b for systolic blood pressure data. Note that the screen 700 can thus present either raw sensor data (optionally being filtered, de-noised, etc.), such as the ECG data, or values calculated from sensor data, such as systolic blood pressure.

In some aspects, the sensor traces 708 can present data from a historical point 712 to a current point 714 or a historical point 718 that can represent a time when the data was last updated. For example, FIG. 7 illustrates the trace 708a as having a current time of 18:20:03, while the sensor readings stop at 18:18:18, the last time ECG data was synchronized. The trace 708b also shows a current time of 18:20:03, while the systolic blood pressure calculations stop at 18:16:03, the time of last synchronization.

In some cases the historical point 712 can be selected so that the sensor data spans a set time period (e.g., two minutes, 10 minutes, etc.). Functionality can be provided to allow a user to scroll to older or newer sensor data 708 (e.g., by swiping left or right), or to change the scale of the display so that a longer or shorter time window is displayed (e.g., using a pinch to zoom gesture). The sensor data 708 can be displayed according to the selected scale, such as placing data points more closely together when a larger scale (e.g., larger time range) is in view.

The sensor traces 708 can be configured to visually convey additional information. For example, the trace 708b can be color coded, or be provided with different line styles or other characteristics, to indicate whether values are in particular ranges, such as good, warning, and bad.

Depending on software and hardware settings and capabilities, the sensor traces 708 can provide real time data. The frequency of data transmissions from a monitoring device can be selected based on various factors, including the range of the device from a receiving device (such as a server or a device carried by medical personnel) and the condition of the patient. For example, the transmission rate can be calculated by considering power, user requirements, and the need for frequent data updates. If the patient is healthy, it may be preferable to send less frequent updates, which can conserve power. Similarly, if the monitoring device can use a lower power transmission mode, more frequent updates may be provided than if a higher power transmission mode is to be used. If sensor readings indicate that the patient's health is deteriorating, transmissions may be sent more frequently, including in real time. In particular examples, a user, such as the user of the monitoring device or a medical professional, can select a rate at which to receive data updates, including whether real time data transmission should be enabled. In other cases, the update rate can be automatically configured, such as based on rules or thresholds.

The screen 700 can convey additional information, including a patient identifier 720 and diagnostic summary information, such as current values for shock 722, heart rate 724, systolic blood pressure 726, respiration rate 728, and peripheral capillary oxygen saturation 730. The screen 700 can also convey a connection status 734 (e.g., how and whether a monitoring device is currently transmitting), a refresh or synchronization indicator 736, and a last synchronization time 738.

Example 6

Computing Environment for Patient Monitoring

Figure 8:
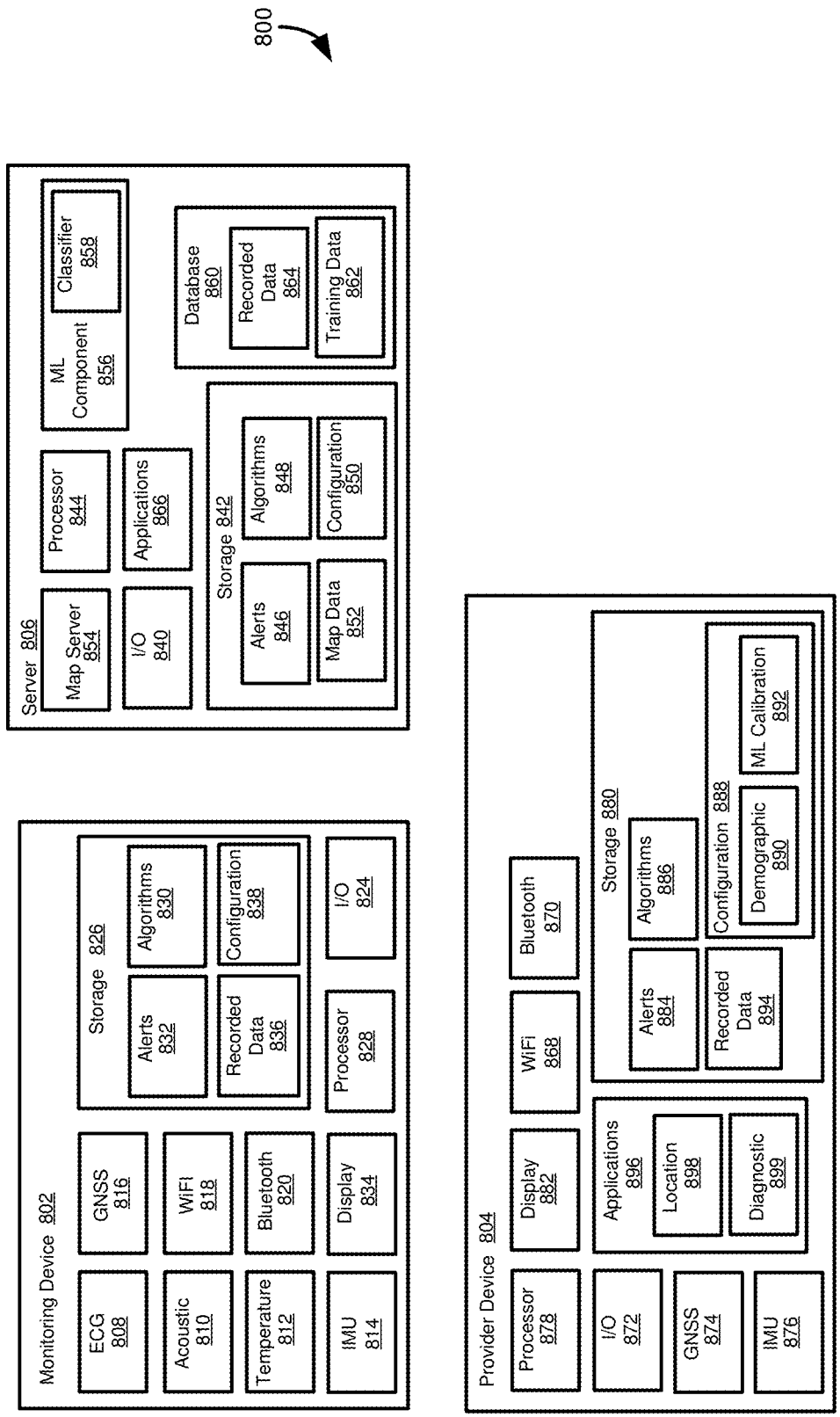
FIG. 8 is a diagram illustrating an example computing environment in which disclosed technologies can be implemented.

FIG. 8 illustrates an example computing environment 800 in which at least certain aspects of the disclosed technologies can be implemented. The computing environment 800 can include a monitoring device 802 and a provider device 804, which may correspond to the monitoring device 110 and the provider device 150 of FIG. 1. The computing environment 800 can also include one or more servers 806, which can be in communication with the monitoring device 802 and the provider device 804. The computing environment 800 can include additional components, such as client devices (not shown). Client devices can be devices located in a provider facility, such as a disaster shelter, clinic, hospital, or emergency vehicle. The client devices can include various features of the provider device 804, and optionally the server 806.

The monitoring device 802 can include components to record, and optionally process, sensor data, and to transmit this data to other computing devices, such as the provider device 804 or the server 806. Sensors can include an ECG sensor 808, an acoustic sensor 810, and a temperature sensor 812. Although described as a "sensor," it should be appreciated that the sensors 808, 810, 812 can incorporate multiple sensor components. For example, the ECG sensor 808 can include a single lead or can include multiple leads, such as three leads or five leads. The acoustic sensor 810 can include a plurality of acoustic detection devices, such as electret microphones. The temperature sensor 812 can include a sensor to detect an ambient temperature and a sensor to detect patient temperature.

The sensors can also include an inertial measurement unit 814, or components typically included in an inertial measurement unit (IMU). The IMU 814 typically includes components such as one or more accelerometers, a magnetometer, and a gyroscope. The magnetometer may be used to determine the orientation of the monitoring device 802 (and, by extension, a monitored individual) about a vertical axis. The gyroscope may be used to measure the tilt of the monitoring device 802 (and, by extension, a monitored individual). The one or more accelerometers may be used to measure movement of the monitoring device 802 (and, by extension, a monitored individual). In a particular example, the one or more accelerometers include a three-axis accelerometer, and accelerometer data can be used to determine a respiration rate for a monitored individual.

The monitoring device 802 can include other types of sensors, or some of the sensors shown in FIG. 8 can be removed from the monitoring device, based on various considerations, including use case scenarios, cost, etc. For example, the monitoring device 802 can include one or more optical sensors, such as for obtaining oximetry data. The optical sensors can include finger mounted devices (including wireless devices that can transmit data, such as oximetry data, to a provider device 804 or another device), or can be based on reflectance techniques, in which case the optical sensors can be incorporated into a housing of the monitoring device 802 or can otherwise be located in close physical proximity to the monitoring device (e.g., on the patient's chest, rather than on their finger).

The monitoring device 802 can include a global navigation satellite system (GNSS) sensor 816. The GNSS sensor 816 can be useful for providing a general location of the monitoring device 802, and therefore the patient. The location of the monitoring device 802 can also be determined, or made more accurate, using other components of the monitoring device, such as a Wi-Fi transceiver 818 or a Bluetooth transceiver 820 (e.g., via triangulation or other methods, such as estimating distance based on signal strength or transit time). The Wi-Fi transceiver 818 and the Bluetooth transceiver 820 may also be used to receive data, such as from the provider device 804 or the server 806, as well as to send data to the provider device or the server.

The monitoring device 802 may include other types of communication components, such as a near-field communication component or a cellular communication component (e.g., to transmit or receive using a LTE network). Although wireless communication is typically preferred, in at least some cases, the monitoring device 802 may be configured to allow for wired communications, such as via a USB connection. Communications involving transceiver components (e.g., the Wi-Fi transceiver 818 and the Bluetooth receiver 820), or optionally sensor components (e.g., the ECG sensor 808, the temperature sensor 812, the IMU 814, or the GNSS sensor 816) can be managed by an input/output (I/O) manager 824. The I/O manager 824 can manage network connections as well as manage hardware interfaces, such as communication busses or I/O pins. Although shown as a single component, the I/O manager 824 can include multiple components, and can be implemented in hardware, software, or a combination thereof.

The monitoring device 802 can include storage 826. The storage 826 can be any suitable storage, but is typically selected to include a relatively low power, high durability storage medium, such as flash memory. The storage 826 can also include volatile memory (e.g., RAM), and other types of non-volatile memory, such as ROM or EEPROM. The storage 826 can be in communication with a processor 828, which can process instructions for managing the other various components of the monitoring device 802, including processing sensor data using algorithms 830 that may be maintained in the storage 826.

The algorithms 830 can include techniques for processing sensor data, such as to clean up sensor signals or to calculate values (e.g., heart rate, blood pressure, shock index, respiration rate) based on sensor data. Alerts 832 can be defined that can be triggered based on values calculated using the algorithms 830 or based directly on sensor measurements. Alerts 832 can include when vital signs fail to satisfy a threshold, such as a blood pressure, temperature, shock index, heart rate, or respiration rate being outside of prescribed range. Typically, if an alert is triggered, a communication is sent, such as to a provider device 804 or the server 806, using the Wi-Fi transceiver 818 or the Bluetooth transceiver 820.

However, in some aspects, alerts can be provided through the monitoring device 802. For example, the monitoring device can include a display 834 on which alerts can be presented. Or, alerts 832 can be indicated by the monitoring device 802 by generating an audio signal (such as using a piezoelectric speaker or an electrodynamic speaker) or another type of visual signal, such as illumination of one or more LED lights. In order to reduce power requirements, cost, and device weight, it can be beneficial to use lower cost audio or visual alert mechanisms on the monitoring device 802. Different types of audio signals or visual signals, including illuminating different numbers of lights, using different colors, or using different patterns, can be used to indicate different alert conditions, as well as convey an alert level (e.g., brighter lights, more lights, more frequent blinking, higher pitch, or higher volume) for a particular alert condition.

The storage 826 can include recorded data 836. The recorded data 836 can be current data or can represent at least a period of historical data. For example, the recorded data 836 can be maintained in a buffer, where data in the buffer is periodically sent, such as to a provider device 804 or a server 806, using the Wi-Fi transceiver 818 or the Bluetooth transceiver 820. Data can also be recorded and stored without the monitoring device 802 being in an active transmission mode. Recorded data 836 may be maintained, at least for a period of time, in order to determine whether an alert 832 should be generated (e.g., if a value changes by a threshold amount) or so that a period of data is available for transmission, such as if an alert is generated or the provider device 804 or the server 806 sends a signal to the monitoring device 802 that data should be transmitted.

The storage 826 can include configuration information 838. The configuration information 838 can include information regarding a monitored individual, such as their height, weight, age, gender, ethnicity, name (or other identifying information, such as a patient ID number or a social security number), and health information (e.g., conditions from which the patient may be suffering or health history information). Configuration information 838 can also include information for use in setting or configuring alerts 832 (e.g., which alerts should be activated, alert thresholds, locations to which alerts should be sent).

Configuration information 838 can include information that can be used in calculating diagnostic values, such as values for blood vessel or heart dimensions that can be used in blood pressure calculations. Such configuration information 838 can also include values provided by a machine learning based classifier for increasing the accuracy of calculated diagnostic information, as will be further described.

The server 806 can include an I/O manager 840. The I/O manager 840 can manage communications with other computing devices, including the monitoring device 802 and the provider device 804, including though various network connections (e.g., Ethernet, Wi-Fi, Bluetooth, cellular data connection, etc., through various components not shown in FIG. 8). The I/O manager 840 can also mediate access to storage 842 by a processor 844. The storage 842 can include non-volatile storage, volatile storage, or a combination thereof. For example, the storage 842 can include RAM, as well as non-volatile storage such as ROM, EEPROM, and secondary storage media (e.g., flash memory, solid state disks, magnetic disks, and the like, as well as cloud-based storage). The storage 842 can include alerts 846, which can include alert definitions, which can be implemented as described for the alerts 832. The alerts 846 can also include alerts received from another device, such as the monitoring device 802 or the provider device 804. Stored alerts relating to a particular patient can be transmitted to other devices, including other provider devices 804 (e.g., as additional or different medical personnel become involved with a patient) and computing devices located at medical facilities, emergency vehicles, command centers, and the like.

The storage 842 can include algorithms 848 and configuration information 850, which can be at least generally similar to the algorithms 830 and the configuration information 838 of the monitoring device 802. The configuration information 850 can include information for a plurality of monitoring devices 802 and monitored individuals. That is, the server 806 can use the configuration information 850 to associate a particular monitoring device 802 with a particular individual, as well as associating provider devices 804 with particular medical personnel.

The storage 842 can include map data 852. The map data 852 can be provided to other computing devices, such as the provider device 804. The map data 852 can include information regarding building locations, roads, and other features, and can be used to help guide a medical provider to the location of a monitored individual. The map data 852 can include information useable to generate route or navigational information, and can access other data sources to provide real time traffic data and other information. The map data 852 can be combined with location data associated with monitoring devices 802, provider devices 804, and other location information, such as the location of emergency vehicles or medical facilities. Map data 852 can be accessed by a map server 854, which can transmit map data (optionally augmented with other information) to other computing devices, such as a provider device 804. The map server 854 can include other functionality, such as performing route calculations or routing functions, or augmenting map data with the locations of monitoring devices 802, provider devices 804, medical personnel, emergency vehicles, medical facilities, and the like.

The server 806 can include a machine learning component 856 that uses machine learning techniques to determine, at least in part, patient diagnostic information, such as blood pressure and indication of cardiac health. The machine learning component 856 can be based on any suitable machine learning technique. In a particular example, the machine learning component 856 can use a recurrent neural network or a non-linear dynamical system generated using cardiac data measurements.

In the case of a recurrent neural network, the machine learning component 856 can include a classifier 858 trained using information in a database 860 (or other source of stored data). The information in the database 860 can include training data 862, which can be data for which a diagnostic value of interest is known and physiological information that is to be correlated with the diagnostic value.

For example, the training data 862 can include ECG or phonocardiographic information and corresponding information regarding diagnostic information such as blood pressure. Thus, the machine learning component 856 can be trained such that given an input, such as ECG readings or phonocardiographic data, the classifier can provide a value for blood pressure.

In further cases, diagnostic information can be determined by means of an equation or algorithm, and the machine learning component 856 can supply a corrective factor to improve the accuracy of the diagnostic values. In such cases, the training data 862 can include other information so that a corrective factor can be made more accurate for particular patients. For example, the training data 862 can include patient demographic information such as gender, age, height, weight, race, medical history, etc. such as that given the demographic information for a particular patient, the estimated blood pressure (or other diagnostic) or correction factor has improved accuracy.

In the case where the machine learning component 856 uses a non-linear dynamic system, the training data can be used to extract one or more equations from which diagnostic information can be calculated. Equations calculated from the machine learning component 856 can be used in the algorithms 848, or transmitted to the monitoring device 802 (e.g., to be included in the algorithms 830), to the provider device 804, or to another computing device.

A particular example, the training data 862 includes one or more of the feature sets of Example 4 of the present disclosure.

The database 860 can include additional information, including recorded data 864. The recorded data 864 can be sensor data or calculated values received from a monitoring device 802. The recorded data 864 can be stored and transmitted to provider devices 804 or other computing devices, and can be recorded for later review. The database 860 can also store information related to particular monitored individuals (e.g., medical record information) and treatment and incident data relating to a situation where a patient was actively being monitored using a monitoring device 802. In some cases, the recorded data 864 can also be used as training data 862.

The server 806 can include one or more applications 866. The applications 866 can be software applications that can facilitate monitoring using the monitoring device 802 and the provider device 804. For example, the applications 866 can provide all or a portion of the functionality describes with respect to the user interface screens 500-700 of FIGS. 5-7. The applications 866 can also include functionality for calculating diagnostic values, including in conjunction with the algorithms 848 and the machine learning component 856. In some cases, the applications 866 can provide the bulk of user functionality of the provider device 804. That is, the server 806 can provide the applications 866 as web applications, for example, which can be accessed via a browser or other interface of the provider device 804 or another computing device. In other cases, the applications 866 can manage the internal functionality of the server 806, including providing data to the provider device 804, but all or the bulk of user functionality of the provider device is provided by the provider device.

The provider device 804 can include various features that are similar to features of the monitoring device 802, and will not be further described. These components include a Wi-Fi transceiver 868, a Bluetooth transceiver 870, an I/O manager 872, a GNSS component 874, and an IMU 876, which can be similar to the corresponding components 818, 820, 824, 816, 814. The components 868, 870, 874, 876 can be used, among other things, to track the location of a medical provider, including to help the medical provider navigate to the location of a monitored individual.

A processor 878 can execute computer-executable instructions for implementing various components and functionalities of the provider device 804, including interfacing with storage 880 and a display component 882. The display component 882 can render various user interface screens, such as the screens 500-700 of FIGS. 5-7 on a hardware display (which can be a touchscreen display, such as a capacitive touchscreen) of the provider device 804.

The storage component 880 can be generally similar to the storage component 826, including the provision of both volatile and nonvolatile storage (including secondary storage, such as flash memory). The storage component 880 can store alerts 884 received by the provider device 804, including so that a user can review the alerts, such as through a display rendered on the display component 882. The storage component 880 can also store algorithms 886, which can be analogous to the algorithms 830 or 848. As can be seen from FIG. 8, diagnostic information can be calculated on different devices, or on multiple (including all) devices in the environment 800. So long as some component of the environment 800 includes a component that is capable of calculations using the algorithms, other components need not include the algorithms, or the algorithms of such component need not be used.

The storage 880 can store configuration information 888. The configuration information 888 can include information identifying a particular user associated with the provider device 804. The configuration information 888 can also include information such as the identities of monitoring devices 802 which the provider device 804 is monitoring and servers 806 in communication with the provider device.

The configuration information 888 can include demographic information 890. The demographic information 890 can provide values for variables based on various demographic properties, such as patient age, height, race, weight, gender, and other factors. As details regarding a monitored individual become known, the information can be used to retrieve appropriate values from the demographic information 890, which can allow more accurate diagnostic results to be calculated. The demographic information 890 can also be used to adjust alerts 884 or other types of status information for a patient. For example, whether a particular diagnostic is a warning sign or not may depend on demographic information of the patient. Machine learning calibration information 892 can also be maintained as part of the configuration information 888 and used to improve the accuracy of calculated diagnostic values, alerts, patient status information, and other patient-related information.

The storage 880 can include recorded data 894. The recorded data 894 can represent historical data received from a monitoring device 802 or a server 806. The recorded data 894 can be useful when a user desires to view older data, or a data window that includes older data.

The provider device can include one or more software applications 896. The software applications 896 can include location functionality 898 and diagnostic functionality 899. The location functionality 898 can correspond to the map section 504, 604 of the screens 500, 600. The diagnostic functionality 899 can correspond to the diagnostic sections 502, 616 of the screens 500, 600.

Example 7

Example Operations for Blood Pressure Determination

Figure 9B:
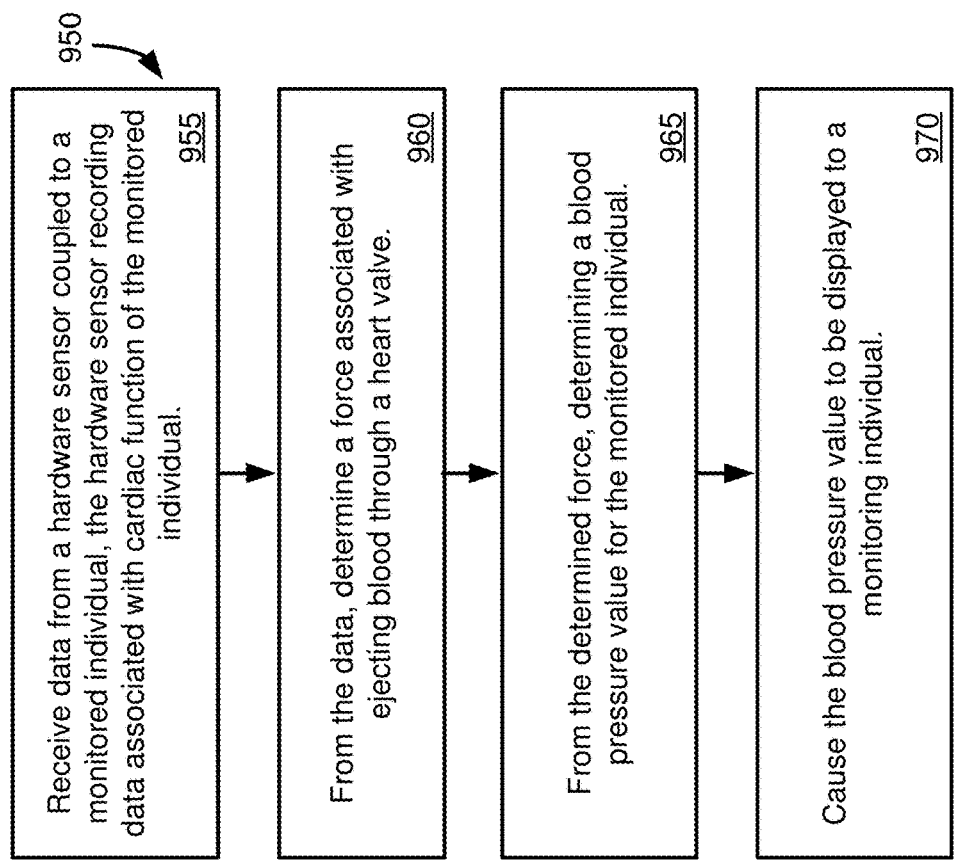
FIG. 9B is a flowchart of a method for determining blood pressure based on blood velocities.
Figure 9A:
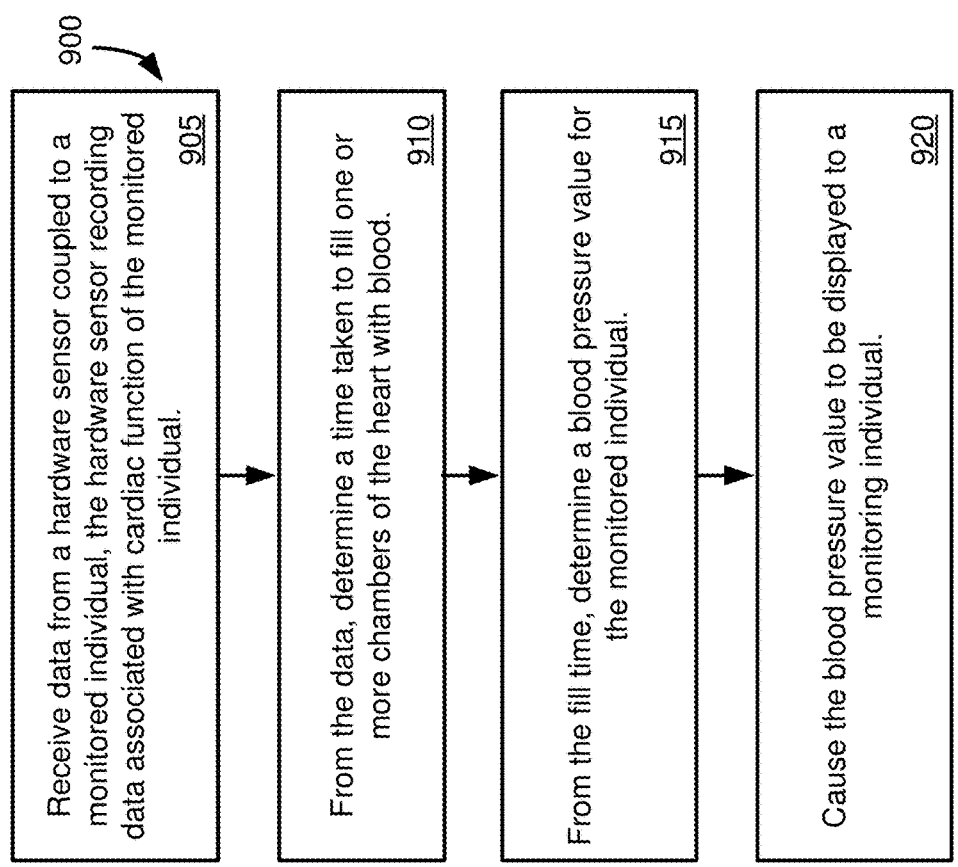
FIG. 9A is a flowchart of a method for determining blood pressure based on heart chamber fill time.

FIG. 9A presents a flowchart of an example method 900 for determining blood pressure of a monitored individual, such as on a continuous basis. The method 900 can be carried out using the computing environment of FIG. 8, can use data features depicted in FIG. 4, and can be carried out, at least in part, using the monitoring device 300 of FIG. 3, a provider device, and/or another device. At 905, data is received from a hardware sensor coupled to a monitored individual. The hardware sensor records data associated with cardiac function of the monitored individual. A sensor coupled to the monitored individual refers to the hardware sensor being in sufficient physical proximity or contact with the monitored individual to obtain clinically useful readings from the sensor.

From the data, a time taken to fill one or more chambers of the heart with blood is determined at 910. At 915, from the fill time, a blood pressure value is determined for the monitored individual. The blood pressure value is caused to be displayed to a monitoring individual at 920. For example, a monitoring device receives 905 data from the hardware sensor coupled to a monitored individual, determines 910 the time taken to fill chamber(s) of the heart with blood, determines 915 the blood pressure value, and causes 920 the blood pressure value to be displayed (e.g., displayed on a screen associated with the monitoring device, or transmitted to another device for display). As another example, a provider device receives 905 data from the hardware sensor coupled to a monitored individual, determines 910 the time taken to fill chamber(s) of the heart with blood, determines 915 the blood pressure value, and causes 920 the blood pressure value to be displayed (e.g., displayed on a screen associated with the provider device, or transmitted to another device for display). Or, as another example, a server device receives 905 data from the hardware sensor coupled to a monitored individual, determines 910 the time taken to fill chamber(s) of the heart with blood, determines 915 the blood pressure value, and causes 920 the blood pressure value to be displayed (e.g., displayed on a screen associated with the server device, or transmitted to another device for display).

FIG. 9B presents a flowchart of an example method 950 for determining blood pressure of a monitored individual, such as on a continuous basis. The method 950 can be carried out using the computing environment of FIG. 8, can use data features depicted in FIG. 4, and can be carried out, at least in part, using the monitoring device 300 of FIG. 3, a provider device, and/or another device. At 955, data is received from a hardware sensor coupled to a monitored individual. The hardware sensor records data associated with cardiac function of the monitored individual. A sensor coupled to the monitored individual refers to the hardware sensor being in sufficient physical proximity or contact with the monitored individual to obtain clinically useful readings from the sensor.

From the data, a force associated with ejecting blood through a heart valve is determined at 960. At 965, from the determined force, a blood pressure value is determined for the monitored individual. The blood pressure value is caused to be displayed to a monitoring individual at 970. For example, a monitoring device receives 955 data from the hardware sensor coupled to a monitored individual, determines 960 the force, determines 965 the blood pressure value, and causes 970 the blood pressure value to be displayed (e.g., displayed on a screen associated with the monitoring device, or transmitted to another device for display). Or, as another example, a provider device receives 955 data from the hardware sensor coupled to a monitored individual, determines 960 the force, determines 965 the blood pressure value, and causes 970 the blood pressure value to be displayed (e.g., displayed on a screen associated with the provider device, or transmitted to another device for display). Or, as another example, a server device receives 955 data from the hardware sensor coupled to a monitored individual, determines 960 the force, determines 965 the blood pressure value, and causes 970 the blood pressure value to be displayed (e.g., displayed on a screen associated with the server device, or transmitted to another device for display).

Example 8

Computing Systems

FIG. 10 depicts a generalized example of a suitable computing system 1000 in which the described technologies may be implemented. The computing system 1000 is not intended to suggest any limitation as to scope of use or functionality, as the technologies may be implemented in diverse general-purpose or special-purpose computing systems.

With reference to FIG. 10, the computing system 1000 includes one or more processing units 1010, 1015 and memory 1020, 1025. In FIG. 10, this basic configuration 1030 is included within a dashed line. The processing units 1010, 1015 execute computer-executable instructions. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 10 shows a central processing unit 1010 as well as a graphics processing unit or co-processing unit 1015. The tangible memory 1020, 1025 may be volatile memory (e.g., registers, cache, RAM), non-volatile memory (e.g., ROM, EEPROM, flash memory, etc.), or some combination of the two, accessible by the processing unit(s). The memory 1020, 1025 stores software 1080 implementing one or more technologies described herein, in the form of computer-executable instructions suitable for execution by the processing unit(s). The instructions can be executed on the processing units 1010 and/or 1015.

A computing system may have additional features. For example, the computing system 1000 includes storage 1040, one or more input devices 1050, one or more output devices 1060, and one or more communication connections 1070. An interconnection mechanism (not shown) such as a bus, controller, or network interconnects the components of the computing system 1000. Typically, operating system software provides an operating environment for other software executing in the computing system 1000, and coordinates activities of the components of the computing system 1000.

The tangible storage 1040 may be removable or non-removable, and includes magnetic disks, magnetic tapes or cassettes, CD-ROMs, DVDs, or any other medium which can be used to store information and which can be accessed within the computing system 1000. The storage 1040 stores instructions for the software 1080 implementing one or more technologies described herein.

The input device(s) 1050 may be a touch input device such as a keyboard, mouse, pen, or trackball, a voice input device, a scanning device, or another device that provides input to the computing system 1000. If the computing system is a monitoring device, the input device(s) 1050 can include an ECG sensor and/or an acoustic sensor. The input device(s) 1050 may be a camera, video card, TV tuner card, or similar device that accepts video input in analog or digital form, or a CD-ROM or CD-RW that reads video samples into the computing system 1000. The output device(s) 1060 may be a display, printer, speaker, CD-writer, or another device that provides output from the computing system 1000.

The communication connection(s) 1070 enable communication over a communication medium to another computing entity, including a disclosed controller. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The technologies can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computer device. In general, a computing system or computer device can be local or distributed, and can include any combination of special-purpose hardware and/or general-purpose hardware with software implementing the functionality described herein.

In various examples described herein, a module (e.g., component or engine) can be "coded" to perform certain operations or provide certain functionality, indicating that computer-executable instructions for the module can be executed to perform such operations, cause such operations to be performed, or to otherwise provide such functionality. Although functionality described with respect to a software component, module, or engine can be carried out as a discrete software unit (e.g., program, function, class method), it need not be implemented as a discrete unit. That is, the functionality can be incorporated into one or more programs, such as one or more lines of code in one or more larger programs, or a general purpose program.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Example 9

Mobile Device

Figure 11:
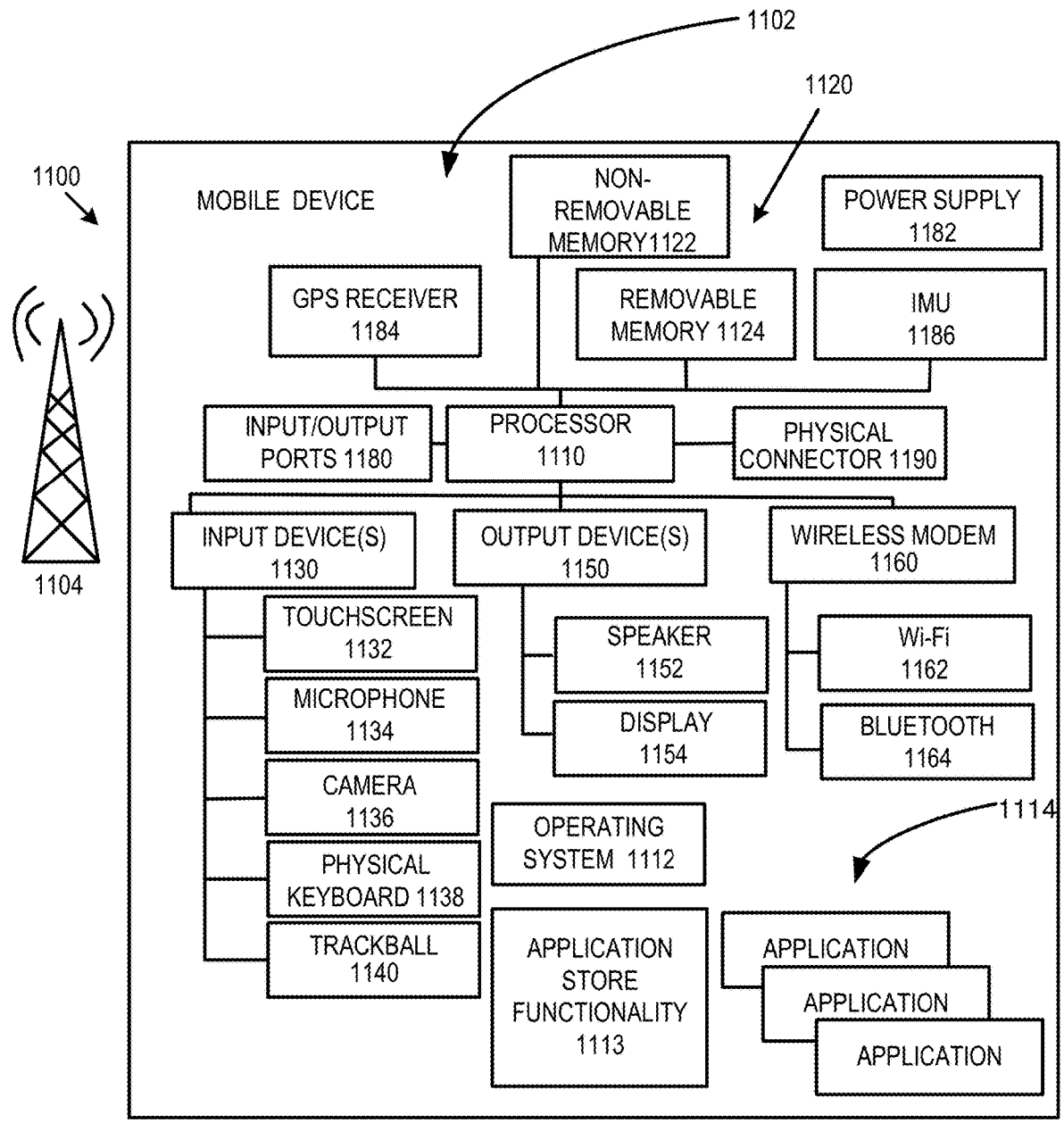
FIG. 11 is an example mobile device that can be used in conjunction with the technologies described herein.

FIG. 11 is a system diagram depicting an example mobile device 1100 including a variety of optional hardware and software components, shown generally at 1102. Any components 1102 in the mobile device can communicate with any other component, although not all connections are shown, for ease of illustration. The mobile device can be any of a variety of computer devices (e.g., cell phone, smartphone, handheld computer, Personal Digital Assistant (PDA), etc.) and can allow wireless two-way communications with one or more mobile communications networks 1104, such as a cellular, satellite, or other network.

The illustrated mobile device 1100 can include a controller or processor 1110 (e.g., signal processor, microprocessor, (application specific integrated circuits) ASIC, or other control and processing logic circuitry) for performing such tasks as signal coding, data processing, input/output processing, power control, and/or other functions. An operating system 1112 can control the allocation and usage of the components 1102 and support for one or more application programs 1114. The application programs can include common mobile computing applications (e.g., email applications, calendars, contact managers, web browsers, messaging applications), or any other computing application (e.g., for calculating and/or monitoring vital signs). Functionality 1113 for accessing an application store can also be used for acquiring and updating application programs 1114.

The illustrated mobile device 1100 can include memory 1120. Memory 1120 can include non-removable memory 1122 and/or removable memory 1124. The non-removable memory 1122 can include RAM, ROM, flash memory, a hard disk, or other well-known memory storage technologies. The removable memory 1124 can include flash memory or a Subscriber Identity Module (SIM) card, which is well known in GSM communication systems, or other well-known memory storage technologies, such as "smart cards." The memory 1120 can be used for storing data and/or code for running the operating system 1112 and the applications 1114. Example data can include web pages, text, images, sound files, video data, or other data sets to be sent to and/or received from one or more network servers or other devices via one or more wired or wireless networks. The memory 1120 can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment.

The mobile device 1100 can support one or more input devices 1130, such as a disclosed controller, a touchscreen 1132, microphone 1134, camera 1136, physical keyboard 1138 and/or trackball 1140 and one or more output devices 1150, such as a speaker 1152 and a display 1154. For a monitoring device, the input devices 1130 can include an ECG sensor and/or acoustic sensor. Other possible output devices (not shown) can include piezoelectric or other haptic output devices. Some devices can serve more than one input/output function. For example, touchscreen 1132 and display 1154 can be combined in a single input/output device.

The input devices 1130 can include a Natural User Interface (NUI). An NUI is any interface technology that enables a user to interact with a device in a "natural" manner, free from artificial constraints imposed by input devices such as mice, keyboards, remote controls, and the like. Examples of NUI methods include those relying on speech recognition, touch and stylus recognition, gesture recognition both on screen and adjacent to the screen, air gestures, head and eye tracking, voice and speech, vision, touch, gestures, and machine intelligence. Other examples of a NUI include motion gesture detection using accelerometers/gyroscopes, facial recognition, 3D displays, head, eye, and gaze tracking, immersive augmented reality and virtual reality systems, all of which provide a more natural interface, as well as technologies for sensing brain activity using electric field sensing electrodes (EEG and related methods). Thus, in one specific example, the operating system 1112 or applications 1114 can comprise speech-recognition software as part of a voice user interface that allows a user to operate the device 1100 via voice commands. Further, the device 1100 can comprise input devices and software that allows for user interaction via a user's spatial gestures, such as detecting and interpreting gestures to provide input to a gaming application. The device 1100 can use a disclosed controller as an input device, in some aspects.

A wireless modem 1160 can be coupled to an antenna (not shown) and can support two-way communications between the processor 1110 and external devices, including a disclosed controller, as is well understood in the art. The modem 1160 is shown generically and can include a cellular modem for communicating with the mobile communication network 1104 and/or other radio-based modems (e.g., Bluetooth 1164 or Wi-Fi 1162). The wireless modem 1160 is typically configured for communication with one or more cellular networks, such as a GSM network for data and voice communications within a single cellular network, between cellular networks, or between the mobile device and a public switched telephone network (PSTN).

The mobile device can further include at least one input/output port 1180, a power supply 1182, a satellite navigation system receiver 1184, such as a Global Positioning System (GPS) receiver, an inertial measurement unit (IMU) 1186 (or one or more components thereof, such as a magnetometer, an accelerometer, or a gyroscope, or similar types of sensors), and/or a physical connector 1190, which can be a USB port, IEEE 1394 (FireWire) port, and/or RS-232 port. The illustrated components 1102 are not required or all-inclusive, as any components can be deleted and other components can be added.

Example 10

Cloud-Supported Environment

Figure 12:
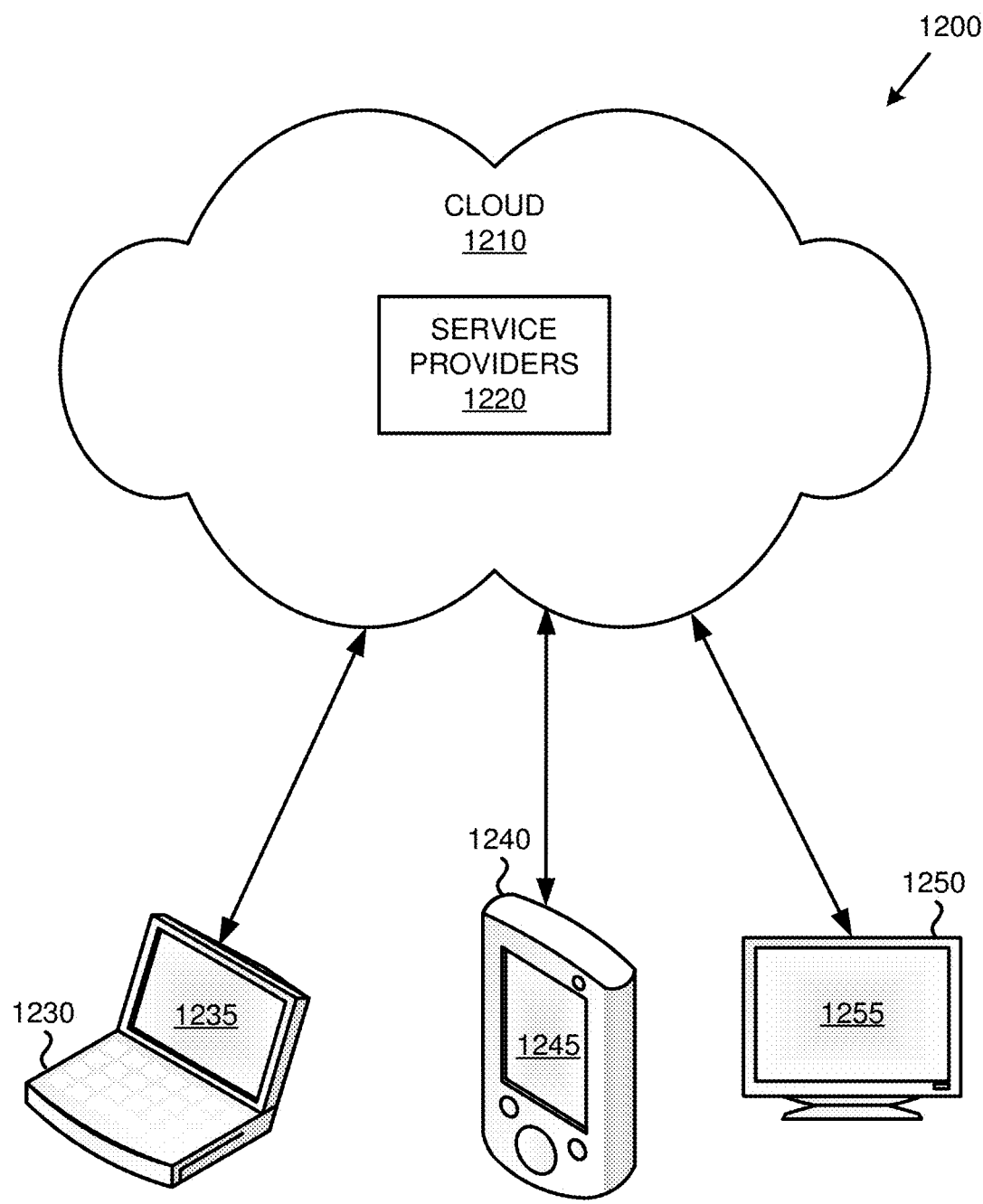
FIG. 12 is an example cloud-support environment that can be used in conjunction with the technologies described herein.

FIG. 12 illustrates a generalized example of a suitable cloud-supported environment 1200 in which described embodiments, techniques, and technologies may be implemented. In the example environment 1200, various types of services (e.g., computing services) are provided by a cloud 1210. For example, the cloud 1210 can comprise a collection of computer devices, which may be located centrally or distributed, that provide cloud-based services to various types of users and devices connected via a network such as the Internet. The implementation environment 1200 can be used in different ways to accomplish computing tasks. For example, some tasks (e.g., processing user input and presenting a user interface) can be performed on local computer devices, while other tasks (e.g., storage of data to be used in subsequent processing) can be performed in the cloud 1210. In example environment 1200, the cloud 1210 provides services for connected devices 1230, 1240, 1250 with a variety of screen capabilities. Connected device 1230 represents a device with a computer screen 1235 (e.g., a mid-size screen). For example, connected device 1230 could be a personal computer such as desktop computer, laptop, notebook, netbook, or the like. Connected device 1240 represents a device with a mobile device screen 1245 (e.g., a small size screen). For example, connected device 1240 could be a mobile phone, smart phone, personal digital assistant, tablet computer, and the like. Connected device 1250 represents a device with a large screen 1255. For example, connected device 1250 could be a television screen (e.g., a smart television) or another device connected to a television (e.g., a set-top box or game console) or the like.

One or more of the connected devices 1230, 1240, 1250 can include touchscreen capabilities. Touchscreens can accept input in different ways. For example, capacitive touchscreens detect touch input when an object (e.g., a fingertip or stylus) distorts or interrupts an electrical current running across the surface. As another example, touchscreens can use optical sensors to detect touch input when beams from the optical sensors are interrupted. Physical contact with the surface of the screen is not necessary for input to be detected by some touchscreens. Devices without screen capabilities also can be used in example environment 1200. For example, the cloud 1210 can provide services for one or more computers (e.g., server computers) without displays.

Services can be provided by the cloud 1210 through service providers 1220, or through other providers of online services (not depicted). For example, cloud services can be customized to the screen size, display capability, and/or touchscreen capability of a particular connected device (e.g., connected devices 1230, 1240, 1250).

In example environment 1200, the cloud 1210 provides the technologies and solutions described herein to the various connected devices 1230, 1240, 1250 using, at least in part, the service providers 1220. For example, the service providers 1220 can provide a centralized solution for various cloud-based services. The service providers 1220 can manage service subscriptions for users and/or devices (e.g., for the connected devices 1230, 1240, 1250 and/or their respective users).

Example 11

Example Implementations

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions or a computer program product stored on one or more computer-readable storage media and executed on a computer device (i.e., any available computer device, including smart phones or other mobile devices that include computing hardware). Computer-readable storage media are tangible media that can be accessed within a computing environment (one or more optical media discs such as DVD or CD, volatile memory (such as DRAM or SRAM), or nonvolatile memory (such as flash memory or hard drives)). By way of example and with reference to FIG. 10, computer-readable storage media include memory 1020 and 1025, and storage 1040. By way of example and with reference to FIG. 11, computer-readable storage media include memory and storage 1120, 1122, and 1124. The term computer-readable storage media does not include signals and carrier waves. In addition, the term computer-readable storage media does not include communication connections, such as 1070, 1160, 1162, and 1164.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and sub combinations with one another. The disclosed methods, apparatus, and systems are not limited to any specific aspect or feature or combination thereof, nor do the disclosed embodiments require that any one or more specific advantages be present or problems be solved.

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology.

What is claimed is:

1. A method comprising:
    placing a monitoring device on a subject, the monitoring device comprising a housing having a front surface and a rear surface, a communication component, and at least one lead connecting at least a first hardware sensor to the monitoring device, wherein the rear surface and the at least one lead are secured to a body of the subject and the at least one hardware sensor comprises an ECG sensor or an acoustic sensor;
    receiving data from the at least a first hardware sensor, the at least a first hardware sensor recording data associated with cardiac function of the subject;
    from the data, determining a time taken to empty one or more chambers of the heart of blood to provide an empty time;
    providing at least one heart dimension parameter, the at least one heart dimension parameter representing a physical dimension of a heart;
    from the empty time and the at least one heart dimension parameter, determining a blood pressure value for the subject;
    transmitting the blood pressure value or the data from the monitoring device to a provider device using the communication component; and
    causing the blood pressure value to be output for display on the provider device to a monitoring individual.

2. The method of claim 1, wherein the sensor data consists of ECG data.

3. The method of claim 1, wherein the sensor data consists of phonocardiographic data.

4. The method of claim 1, wherein the empty time is determined based on a difference between a time at which ventricular contraction begins and a time of onset of ventricular/atrial relaxation.

5. The method of claim 1, wherein the blood pressure value is determined as:

$$\text{Pressure} = \frac{256 \, L\eta SV}{\frac{3}{4}\pi r^4 T_{Fill}}$$

where $\eta$ is blood viscosity (in mmHg), L is the length of the aorta (m), SV is the stroke volume (m$^3$), r is the aortic radius (m), and $T_{Fill}$ is the ventricular empty time.

6. The method of claim 5, further comprising applying a correction factor to the blood pressure value, the correction factor being determined using a machine learning algorithm.

7. The method of claim 1, further comprising:
    measuring acoustic signals produced by the subject's heart;
    determining a stroke volume correction factor from the measured acoustic signals; and
    applying the stroke volume correction factor to the blood pressure value.

8. A method comprising:
    placing a monitoring device on a subject, the monitoring device comprising a housing having a front surface and a rear surface, a communication component, and at least one lead connecting at least a first hardware sensor to the monitoring device, wherein the rear surface and the at least one lead are secured to a body of the subject and the at least one hardware sensor comprises an ECG sensor or an acoustic sensor;

receiving data from the at least a first hardware sensor, the at least a first hardware sensor recording data associated with cardiac function of the subject;

by the monitoring device, from the data, determining a time taken to empty one or more chambers of the heart of blood to provide an empty time;

by the monitoring device, from the empty time and at least one heart dimension parameter stored by the monitoring device, the at least one heart dimension parameter representing a physical dimension of a heart, determining a blood pressure value for the subject;

transmitting the blood pressure value from the monitoring device to a provider device using the communication component; and causing the blood pressure value to be output for display on the provider device to a monitoring individual.

9. The method of claim 8, wherein the sensor data consists of ECG data.

10. The method of claim 8, wherein the sensor data consists of phonocardiographic data.

11. The method of claim 8, wherein the empty time is determined based on a difference between a time at which ventricular contraction begins and a time of onset of ventricular/atrial relaxation.

12. The method of claim 8, wherein the blood pressure value is determined as:

$$\text{Pressure} = \frac{256\, L\eta SV}{\frac{3}{4}\pi r^4 T_{Fill}}$$

where η is blood viscosity (in mmHg), L is the length of the aorta (m), SV is the stroke volume (m³), r is the aortic radius (m), and $T_{Fill}$ is the ventricular empty time.

13. The method of claim 12, further comprising applying a correction factor to the blood pressure value, the correction factor being determined using a machine learning algorithm.

14. The method of claim 8, further comprising:
measuring acoustic signals produced by the subject's heart;
determining a stroke volume correction factor from the measured acoustic signals; and
applying the stroke volume correction factor to the blood pressure value.

15. A method comprising:
placing a monitoring device on a subject, the monitoring device comprising a housing having a front surface and a rear surface, a communication component, and at least one lead connecting at least a first hardware sensor to the monitoring device, wherein the rear surface and the at least one lead are secured to a body of the subject and the at least one hardware sensor comprises an ECG sensor or an acoustic sensor;

receiving data from the at least a first hardware sensor, the at least a first hardware sensor recording data associated with cardiac function of the subject;

transmitting the data from the monitoring device to a provider device using the communication component;

at the provider device, from the data, determining a time taken to empty one or more chambers of the heart of blood to provide an empty time;

at the provider device, from the empty time and at least one heart dimension parameter stored on the provider device, the at least one heart dimension parameter representing a physical dimension of a heart, determining a blood pressure value for the subject; and causing the blood pressure value to be output for display on the provider device to a monitoring individual.

16. The method of claim 15, wherein the sensor data consists of ECG data.

17. The method of claim 15, wherein the sensor data consists of phonocardiographic data.

18. The method of claim 15, wherein the empty time is determined based on a difference between a time at which ventricular contraction begins and a time of onset of ventricular/atrial relaxation.

19. The method of claim 15, wherein the blood pressure value is determined as:

$$\text{Pressure} = \frac{256\, L\eta SV}{\frac{3}{4}\pi r^4 T_{Fill}}$$

where η is blood viscosity (in mmHg), L is the length of the aorta (m), SV is the stroke volume (m³), r is the aortic radius (m), and $T_{Fill}$ is the ventricular empty time.

20. The method of claim 19, further comprising applying a correction factor to the blood pressure value, the correction factor being determined using a machine learning algorithm.

21. The method of claim 15, further comprising:
measuring acoustic signals produced by the subject's heart;
determining a stroke volume correction factor from the measured acoustic signals; and
applying the stroke volume correction factor to the blood pressure value.

* * * * *